(12) United States Patent
Ciarlante

(10) Patent No.: US 10,684,630 B1
(45) Date of Patent: Jun. 16, 2020

(54) PORTABLE BEVERAGE DISPENSER FOR AUTOMATIC CONTROL OF NUTRITIONAL INTAKE

(71) Applicant: Victor Ciarlante, Clinton, NJ (US)

(72) Inventor: Victor Ciarlante, Clinton, NJ (US)

( * ) Notice: Subject to any disclaimer, the term of this patent is extended or adjusted under 35 U.S.C. 154(b) by 108 days.

(21) Appl. No.: 15/722,553

(22) Filed: Oct. 2, 2017

Related U.S. Application Data

(60) Provisional application No. 62/403,167, filed on Oct. 2, 2016.

(51) Int. Cl.
| | | |
|---|---|---|
| *B65D 85/72* | (2006.01) | |
| *G05D 7/06* | (2006.01) | |
| *A61J 7/00* | (2006.01) | |
| *B65D 47/06* | (2006.01) | |
| *B65D 47/20* | (2006.01) | |
| *B65D 77/28* | (2006.01) | |

(52) U.S. Cl.
CPC .......... *G05D 7/0635* (2013.01); *A61J 7/0038* (2013.01); *B65D 47/06* (2013.01); *B65D 47/20* (2013.01); *B65D 77/28* (2013.01); *B65D 85/72* (2013.01)

(58) Field of Classification Search
CPC ............... C12Q 1/6827; C12Q 1/6837; C12Q 2537/143; C12Q 2563/131; C12Q 2563/143; C12Q 2565/537; C12Q 1/6855; C12Q 1/6874; C12Q 1/6883; C12Q 1/6886; C12Q 2600/156; G16B 30/00
See application file for complete search history.

(56) References Cited

U.S. PATENT DOCUMENTS

| | | | | |
|---|---|---|---|---|
| 7,762,181 | B2 * | 7/2010 | Boland | A47J 31/40 99/321 |
| 8,290,615 | B2 * | 10/2012 | Crisp, III | B67D 1/0021 700/236 |
| 9,167,928 | B2 | 10/2015 | Hanners | |
| 9,364,109 | B2 | 6/2016 | Paukovits | |
| 9,792,409 | B2 * | 10/2017 | Wernow | G06F 19/3418 |
| 2006/0081653 | A1 * | 4/2006 | Boland | A47J 31/40 222/243 |
| 2006/0151529 | A1 * | 7/2006 | Crisp, III | B67D 1/0057 222/129.1 |

(Continued)

*Primary Examiner* — Kidest Bahta

(57) ABSTRACT

An apparatus to regulate the flow of a liquid from a container, dependent on nutritional requirements of a user stored within computer memory includes a container that comprises a bottom, a body and a lid, the lid including an opening therethrough, a straw or spout for removing the liquid from the container in the lid, a control assembly including a microprocessor, a liquid regulating valve, a port for communicating with an external computing device and source of electrical power. User nutritional information includes a personal profile, beverage list, nutrient limits and dietary, nutrition and hydration goals. Reference data includes beverage composition, recommended nutrient limits, and standards for determining liquid consumption. Sensors to determine temperature, volume, attitude and power level may be included. A method to regulate flow of a liquid from a container, dependent on the dietary, nutritional, medicinal and therapeutic requirements, and hydration goals of a user is disclosed.

20 Claims, 16 Drawing Sheets

(56) References Cited

U.S. PATENT DOCUMENTS

| | | | |
|---|---|---|---|
| 2007/0222619 A1* | 9/2007 | Moran | G01F 1/075 340/573.1 |
| 2010/0266995 A1* | 10/2010 | Gordon | G06Q 99/00 434/127 |
| 2013/0319915 A1* | 12/2013 | Gellibolian | C02F 1/002 210/87 |
| 2014/0303790 A1 | 10/2014 | Huang | |
| 2015/0182797 A1* | 7/2015 | Wernow | G06F 19/3418 434/247 |
| 2016/0143583 A1* | 5/2016 | Jeukendrup | G01F 1/68 600/301 |
| 2017/0340147 A1* | 11/2017 | Hambrock | A47G 19/2227 |

* cited by examiner

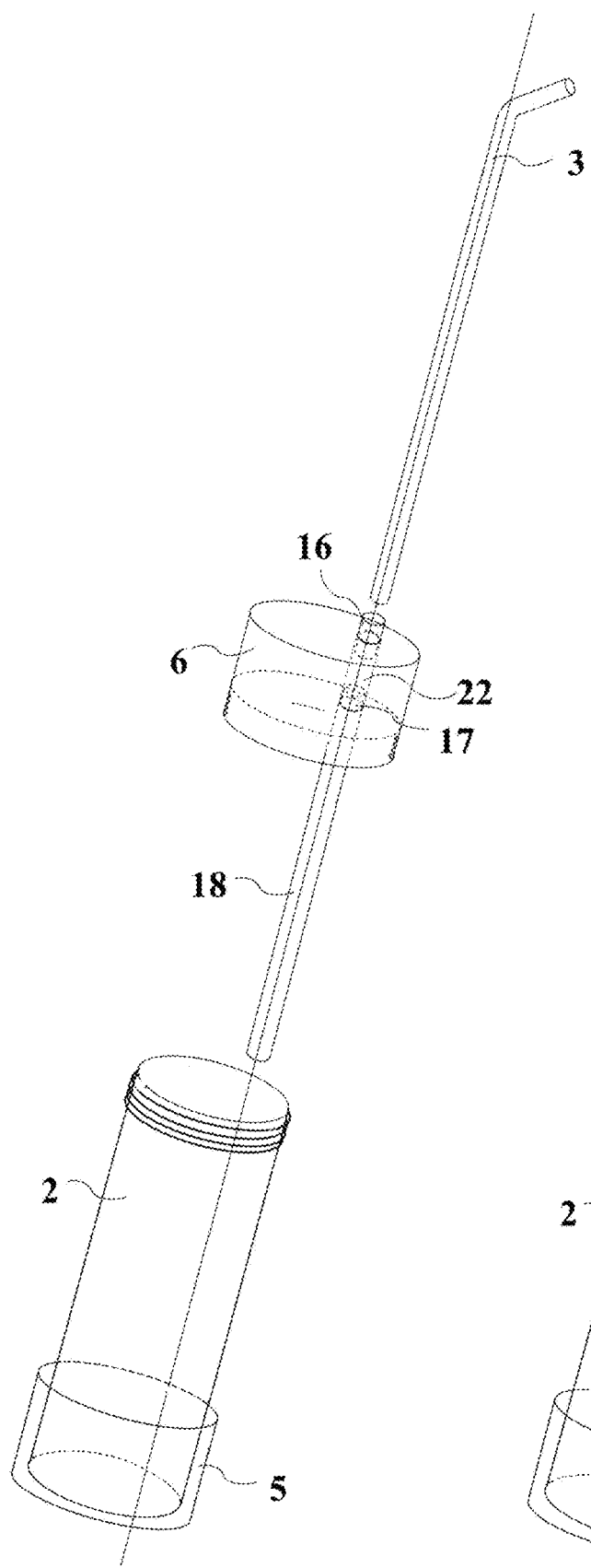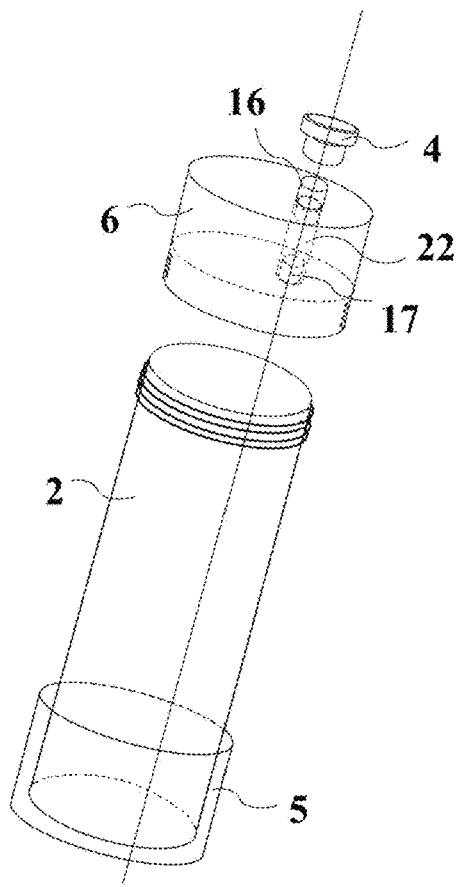
FIG. 6A
FIG. 6B

Full Open Position

Partial Open Position

Fully Closed Position

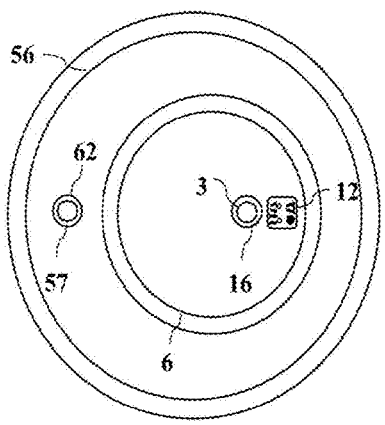
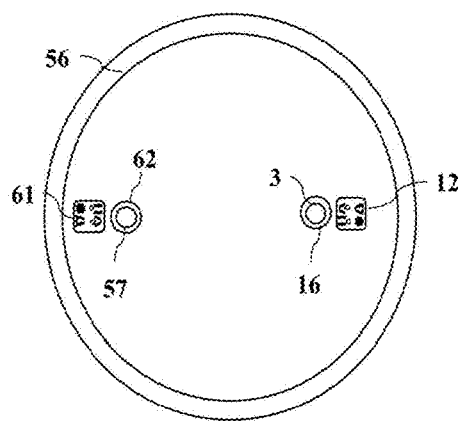
FIG. 10B
FIG. 11B
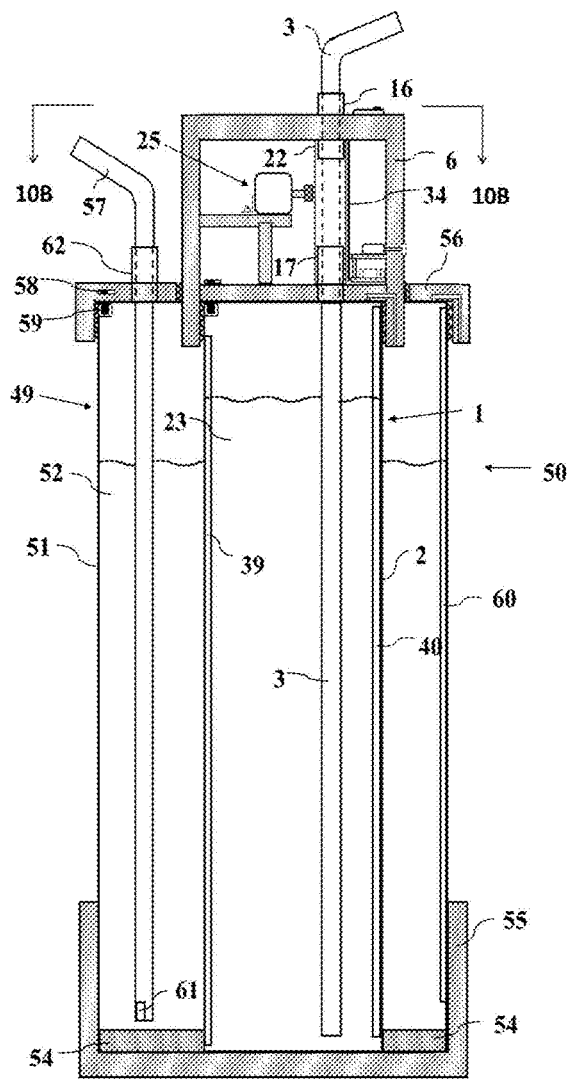
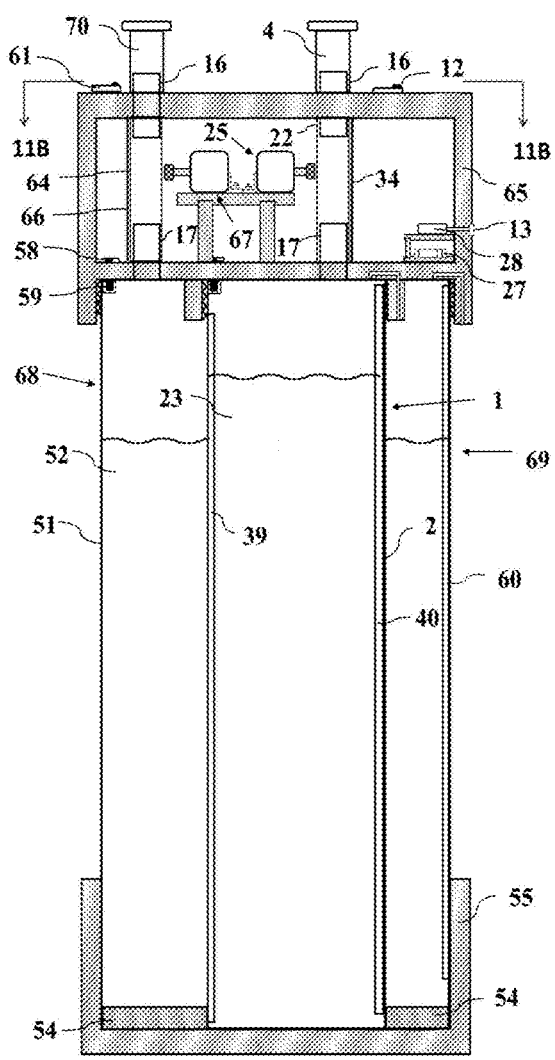
FIG. 10A
FIG. 11A

PORTABLE BEVERAGE DISPENSER FOR AUTOMATIC CONTROL OF NUTRITIONAL INTAKE

CROSS-REFERENCE TO RELATED APPLICATIONS

This application claims the benefit of U.S. Provisional Application Ser. No. 62/403,167, filed 2 Oct. 2016, by the present inventor, and whose contents are incorporated by reference herein in their entirety.

FIELD OF INVENTION

The present invention relates to an automatic portable liquid dispenser, alone or in combination with one or more fluid containers, for controlling and managing the personal consumption of water, calories, sugar, caffeine, nutrients, and other constituents associated with consumption of hot or cold liquids. Embodiments of the present invention may be used for several purposes, including but not limited to dietary and nutritional management, caffeine management, rationing of water and other liquids, personal hydration and fitness, drink behavior training, and medical and therapeutic treatments.

BACKGROUND OF THE INVENTION

The high incidence of obesity amongst adults and children has become a major issue in the U.S. and other countries. On average, Americans consume more calories on a daily basis than is recommended by health experts. A large majority of those additional daily calories come from consuming sugary beverages such as sodas and juices. The options currently in practice to reduce calorie intake from consumption of beverages are: a) replace sugar or glucose in beverages with artificial sweeteners, b) drink beverages that have a reduced sugar content, c) eliminate altogether the consumption of sugary or high calorie beverages, and d) limit the daily intake of sugary drinks to a level recommended by health experts. Artificial sweeteners create an unpleasant taste experience for many people and medical research indicates that they may increase weight gain and the likelihood of developing certain diseases if taken frequently and over an extended duration. Beverages that contain lower sugar content can also provide an unpleasant or unfulfilling taste experience for many people, and are often more expensive than traditional sodas and juices. Research studies have indicated that drinking small quantities of sugary drinks, maintained within recommended limits, are normally not detrimental for otherwise healthy individuals. However, for many people, especially children, relying on will power alone to control or moderate their daily intake of sugary drinks is challenging and often not a practical and sustainable goal.

In addition to calories and sugar, there are other constituents in beverages, such as caffeine and sodium, that if ingested in large enough quantities can negatively impact health or contribute to an unhealthy lifestyle. By using the mandatory nutrient data labeling on beverage containers, for example, it is possible for individuals to track their daily consumption of calories and nutrients, and to take corrective action if cumulative levels exceed personal or recommended daily limits. In theory, a person can maintain a daily written record of liquid volume consumed, and then calculate the corresponding calories and nutrient quantities being consumed from each beverage. However, this "manual" method requires a deep commitment in time and is often difficult to do correctly in a routine and consistent fashion, making it an impractical and unsustainable approach to the problem. Besides the inherent difficulties in monitoring one's liquid intake of calories and nutrients, there is the even greater challenge of correcting and controlling personal drink behavior that may be detrimental to a person's short and long term health and well-being. For parents, caretakers or caregivers, and individuals to accomplish this on a regular basis requires extensive discipline, will power, training, and supervision. This is particularly true for young children and for patients that must limit their daily intake of fluids such as individuals on dialysis and people that have experienced heart failure.

The amount and rate at which individuals consume water, sugary drinks, and other beverages in a single sip (or swallow) or with multiple sips over several seconds or minutes can also contribute to an unsafe and less enjoyable drink experience. Drinking water or other beverages in large swallows and/or too quickly ("chugging" or "gulping") may place undue strain on internal organs, such as kidneys, and can cause sodium levels in the blood to drop to unhealthy or dangerous levels. In extreme and rare cases, drinking too much water in too short of a time period can lead to death—a condition known as Water Intoxication. Drinking too quickly can also pose an unsafe situation with medical patients that have difficulty swallowing, are prone to choking and aspiration (drawing liquid into the lungs), or require special assistance and monitoring when drinking fluids. In hot weather or when very thirsty, children and adults may drink sodas and juices too quickly, in successive sips with no breaks other than to take a breath of air. Besides increasing the likelihood of choking and creating bad drink habits, drinking too quickly can also diminish the enjoyment of consuming a tasty beverage, since a large portion of the liquid is swallowed instead of coming into contact with taste buds in the mouth.

The present invention helps individuals manage their daily liquid intake of water and calories, caffeine, nutrients, and other constituents in beverages by automatically monitoring and controlling the amount, frequency, and rate at which sugary drinks and other beverages can be consumed through a drinking straw or mouthpiece. In addition, the present invention is capable of being used in other useful ways, including but not limited to: rationing water over a finite time interval in cases where access to clean water supply is limited; for transitioning young children from sippy cups to straws; to teach and train children, adolescents and adults how to drink beverages in a healthier and more enjoyable manner; to regulate both the volume and rate at which medical patients consume water, beverages, and medicinal liquids; to regulate liquid consumption by domesticated animals during transit and while in habitat.

US20140303790A1 describes a liquid management system that utilizes gyroscopic sensors, to estimate and track the consumption of pollution index and nutrient index contained in a beverage being consumed by a person. The system compares the information being tracked against recommended limits and provides notifications via Light Emitting Diodes on the drink container.

In U.S. Pat. No. 9,364,109B2, an apparatus is described for controlling liquid volume dispensed from a hand-held container, utilizing a piston to transfer liquid from a reservoir to an individual sucking on a straw. The piston moves axially via the suction force created by the individual sucking on the straw and with the aid of a spring. To fill or re-fill the reservoir with liquid, a pump or other similar conveying method is required to transfer liquid from an external source to the hand-held container.

U.S. Pat. No. 9,167,928 provides a method for limiting the rate of liquid consumption to prevent medical patients from swallowing liquids at too fast of a rate, which may lead to choking and possible aspiration. The method involves the insertion of valve and sealing components within the interior section of a straw that function together to prevent liquid flow when a patient sucks on a straw with excessive force. Valve components of different sizes are required depending on the density of the fluid or beverage being consumed. A caretaker must remove and insert different valve components if a patient drinks varying fluids.

Prior art has focused on hydration and nutrition tracking devices to monitor hydration levels and nutritional intake from food and beverages, and to notify the user if he/she is not consuming a sufficient amount of water, or if the user is eating or drinking too often or too quickly. By providing individuals and caretakers the ability to automatically regulate and modify unhealthy drink behavior to meet specific nutritional and hydration goals, the present invention takes a significant step beyond merely monitoring an individual's daily intake of water and nutrients. The present invention allows individuals to automatically monitor and regulate the frequency, volume, and rate of liquid consumption to aid in achieving a healthier lifestyle, safe hydration, train and improve drink habits, and provide a more pleasurable drink experience. Additionally, the design and construction of the present invention provides spill-free operation and a high degree of portability and ease of use, such as use of standard drinking straws and a conventional gravity assist method in the liquid filling process.

BRIEF DESCRIPTION OF THE SEVERAL VIEWS OF THE DRAWINGS

The accompanying drawings, which are incorporated herein and form part of the specification, illustrate some, but not the only or exclusive, examples of embodiments and/or features which may be configured pursuant to this disclosure. It is intended that the embodiments and figures disclosed herein are to be considered illustrative rather than limiting. In the drawings:

FIG. 2A describes how a customized beverage list is created;

FIG. 2B describes the creation of a user profile;

FIG. 2C describes the monitoring of nutrient consumption and hydration;

FIG. 2D describes controlling nutrient consumption and hydration;

FIG. 5A shows an elevation view of the dispenser lid shown in FIG. 4, with straw attached;

FIG. 5B shows a top view of the dispenser lid shown in FIG. 4, with straw attached;

FIG. 5C shows an elevation view of the dispenser lid shown in FIG. 4, with mouthpiece attached;

FIG. 5D shows a top view of the dispenser shown in FIG. 4, with mouthpiece attached;

FIG. 5E is an alternative embodiment of the present invention showing a plan view of the user interface shown in FIG. 4;

FIG. 6A-B are perspective views of an assembly method for the first embodiment of the present invention, with straw (FIG. 6A) or mouthpiece (FIG. 6B);

FIG. 8B-C shows elevation and plan view of the dispenser in a full open position, FIG. 8D-E shows elevation and plan views of the dispenser in a partial open position;

FIG. 8F-G shows an elevation and plan views of the dispenser in a full closed position;

FIG. 9A-B shows elevation and plan views of the dispenser in a vertical and full closed position;

FIG. 9C shows an elevation view of the dispenser in a tilted and partial open position;

FIG. 9D shows an elevation view of the dispenser in a tilted and full open position;

FIG. 10A-B are elevation and plan views of a liquid container surrounded by a second liquid container, with drink behavior control applied to the inner container;

FIG. 11A-B are elevation and plan views of a liquid container surrounded by a second liquid container, with drink behavior control applied to both containers;

FIG. 12A shows the sip reservoir being filled, while the dispenser, with straw, is in full closed drinking position;

FIG. 12B shows the sip reservoir isolated from the main liquid container, while the dispenser, with straw, is in full open drinking position;

FIG. 12C shows the sip reservoir being filled, while the dispenser, with mouthpiece, is in full closed drinking position;

DETAILED DESCRIPTION OF THE INVENTION

Figure 1A:
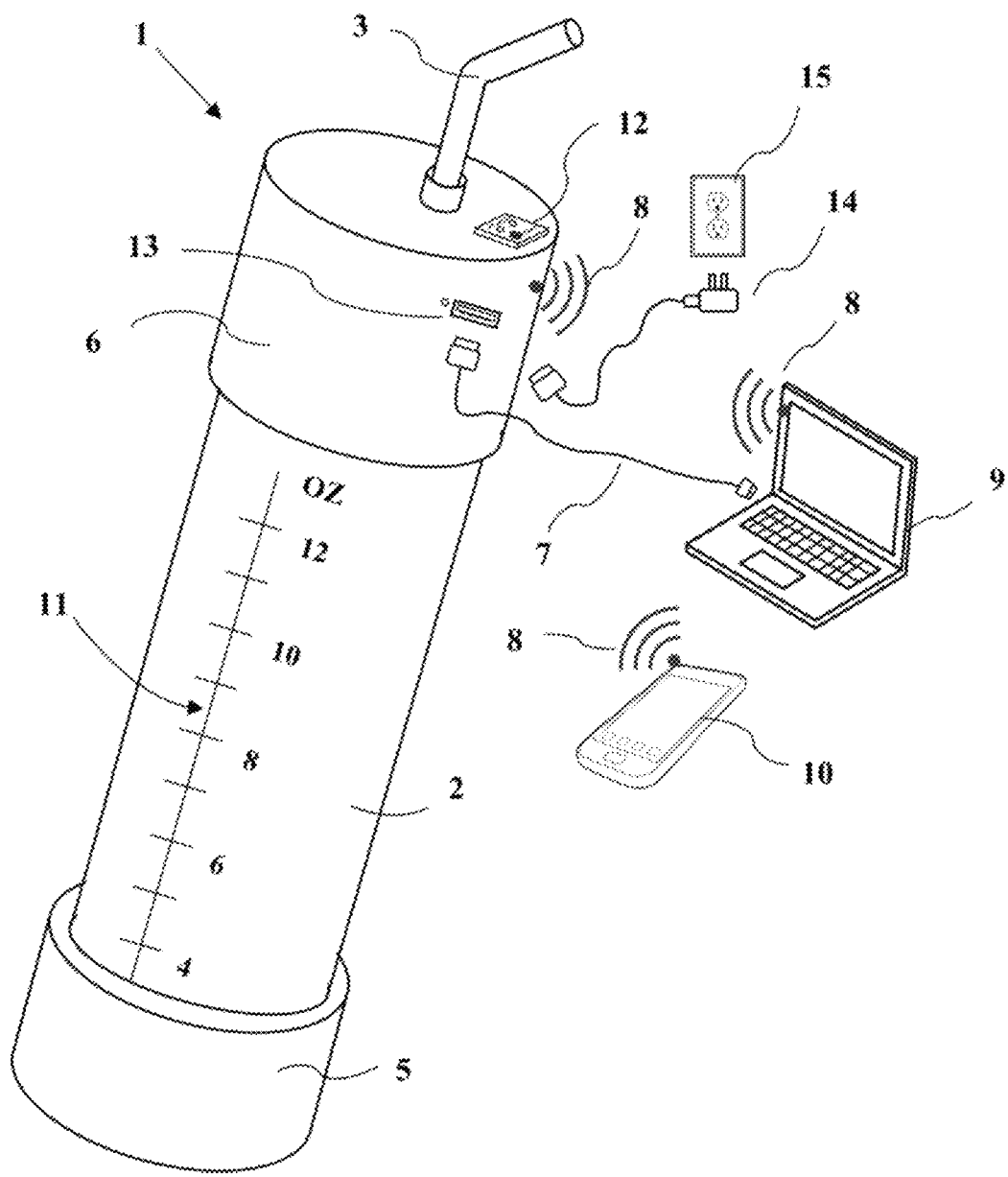
FIG. 1A-B are perspective views of a first embodiment of the present invention with straw fully inserted (FIG. 1A) or a mouthpiece attached (FIG. 1B), and depicting multiple means of communication with external devices.
Figure 1B:
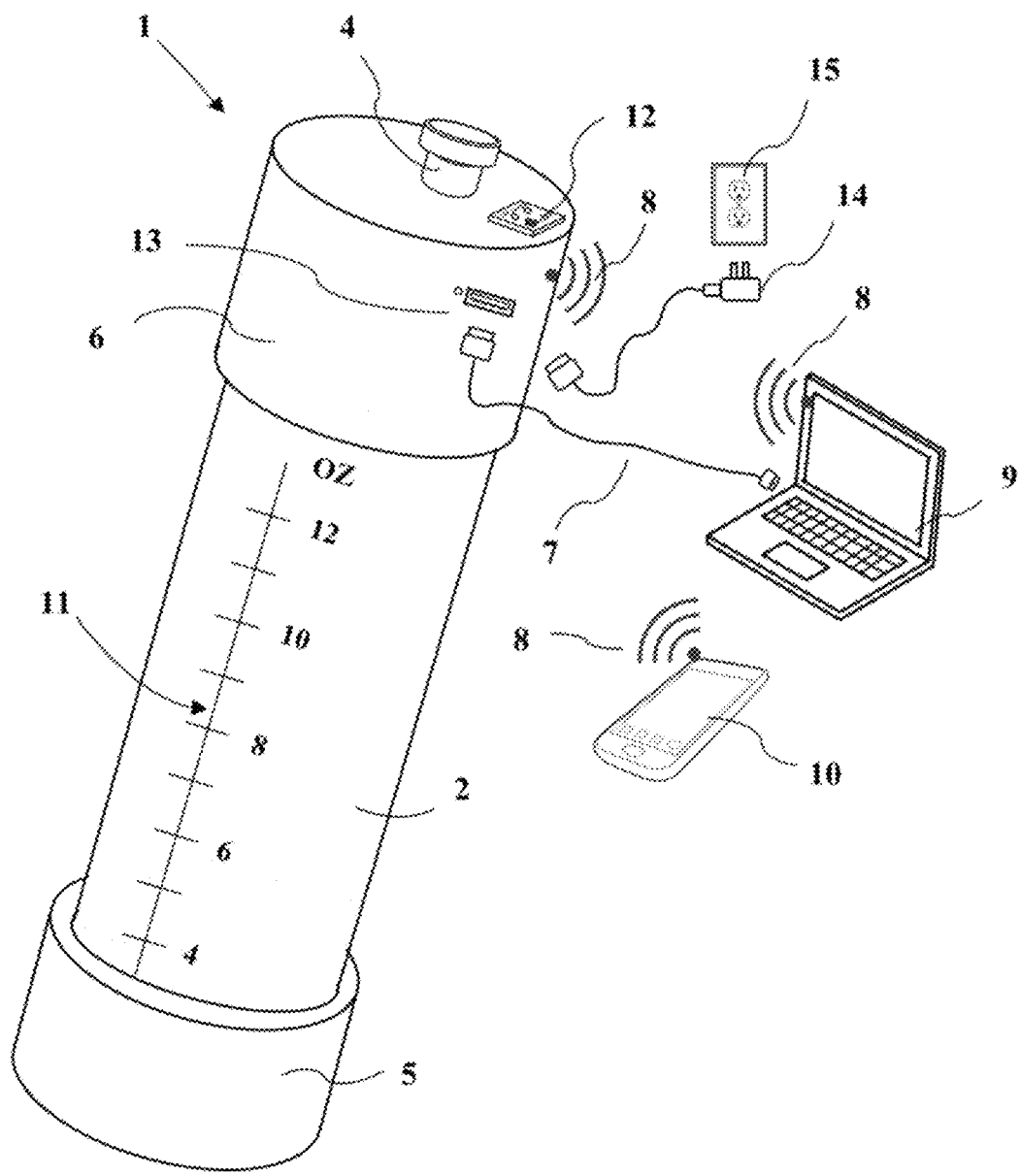
Figure 2A:
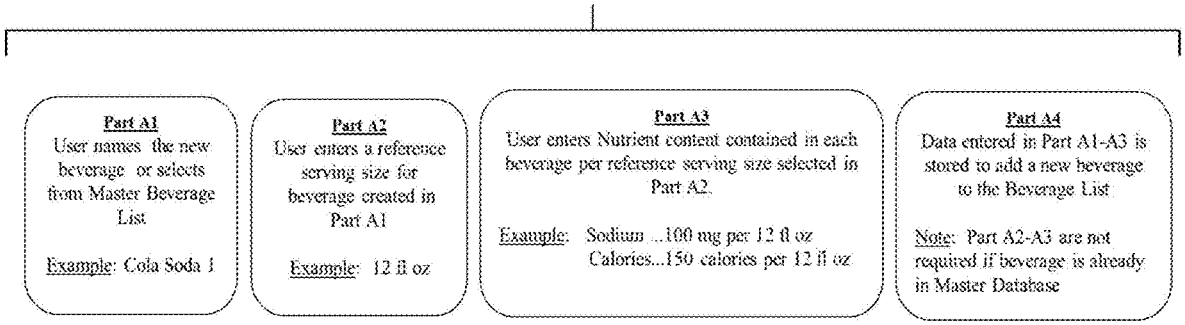
FIG. 2A-D describe the method of a first embodiment of the present invention for monitoring and controlling a user's intake of nutrients.
Figure 2B:
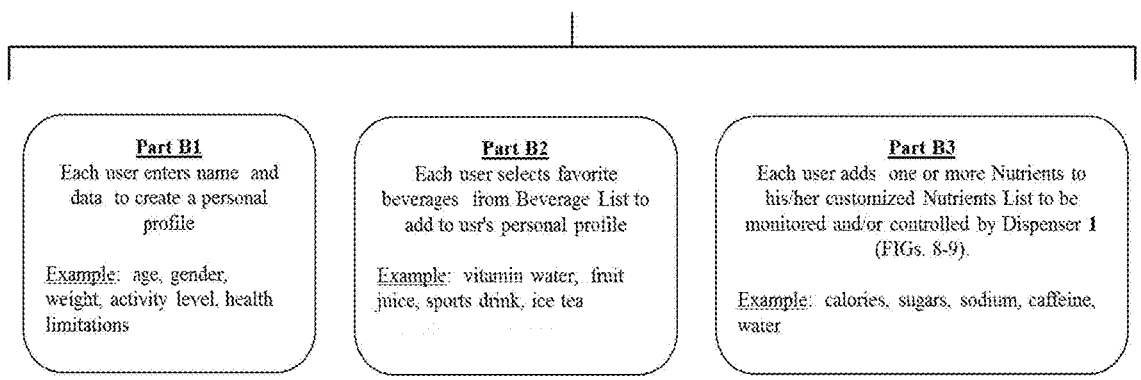
Figure 2B:
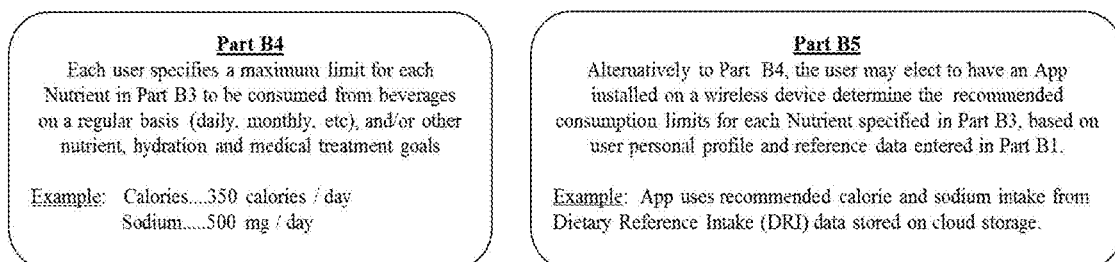
Figure 2C:
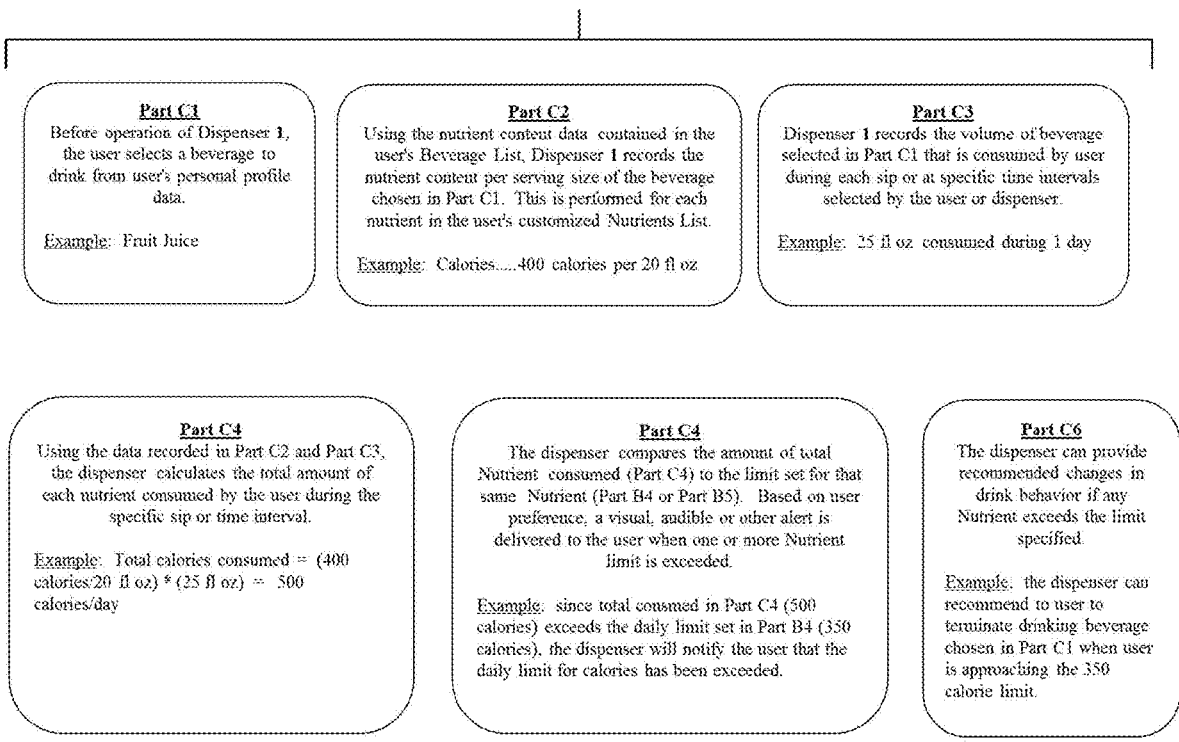
Figure 2D:
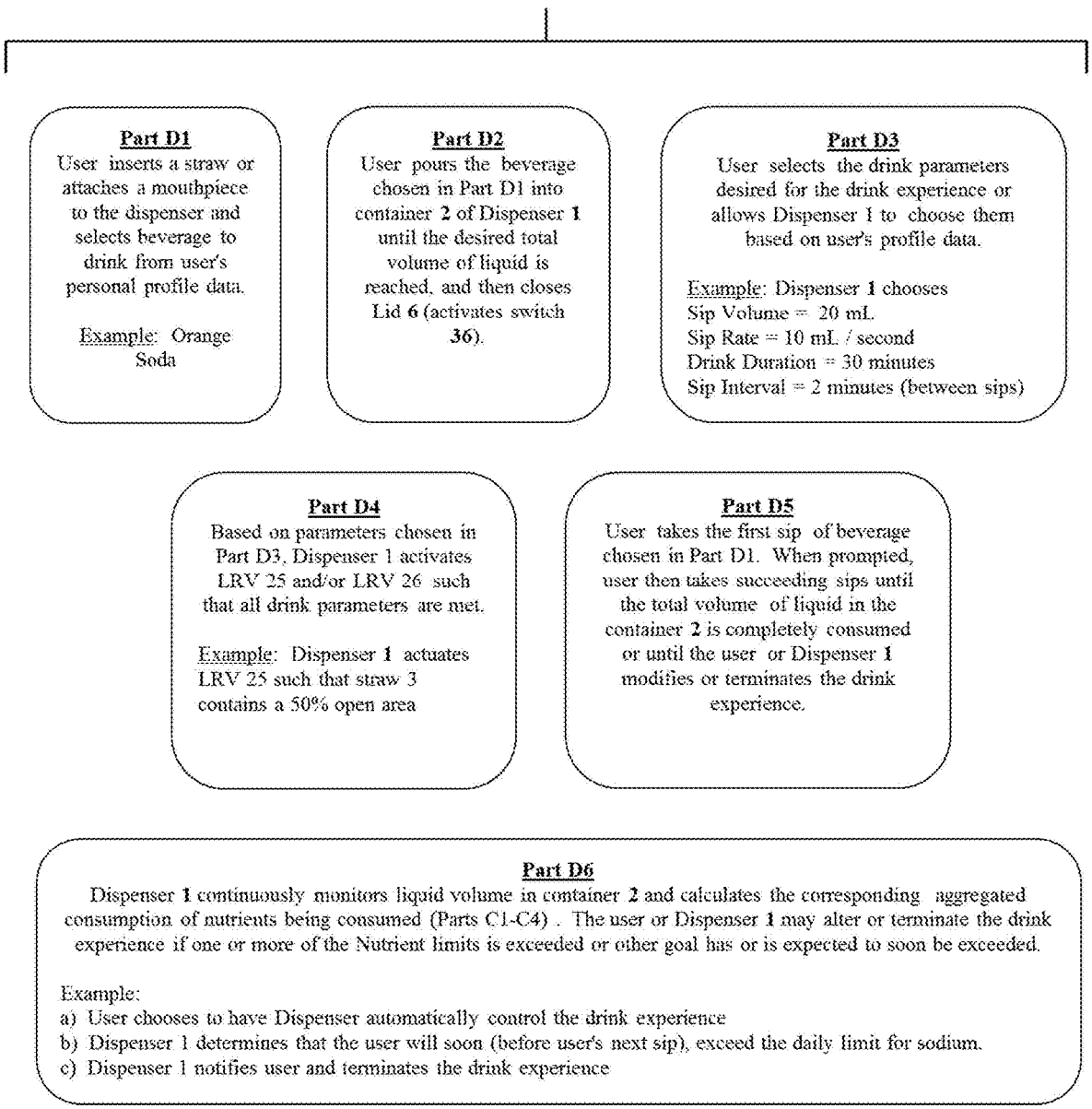

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

The present invention relates broadly to an automatically controlled Portable Beverage Dispenser ("dispenser") and methods for managing an individual's intake of substances such as, for example, water, calories, nutrients, and/or caffeine through the daily or frequent consumption of beverages. Embodiments of the present invention provide a person the ability to automatically monitor, limit, and regulate an individual's intake of calories, nutrients, caffeine, and other constituents contained in sugary drinks and other beverages by controlling the frequency at which sips are taken, as well as adjusting the rate of flow and volume of each sip or sips of beverage consumed by the individual during one or more drink experiences. Embodiments of the present invention may enhance the enjoyment of an individual's overall drink experience and may also be employed in several applications, including but not limited to, controlling nutritional intake, water and liquid rationing, personal hydration and fitness, early childhood drink training, medical and therapeutic treatments, and controlling hydration and nutritional intake for domesticated animals or animals in captivity.

A "user" (for purposes of this specification) includes a person who is consuming the beverage or parent, guardian, or caretaker of the person consuming the beverage. A user can also be an animal (domesticated or in captivity) that is consuming the beverage or caretaker of the animal that is consuming the beverage.

A "beverage" is defined as any liquid that is consumed by a user for any purpose including but not limited to: hydration, for example water and sports drinks; for recreational use, for example "sugary drinks" such as sodas (soft drinks) and juices; for energy boost or alertness, for example caffeinated beverages such as coffees and teas; and for medicinal or therapeutic uses, for example a beverage or liquid that contains medicine that is consumed by patients. A beverage can be either carbonated or non-carbonated, and can be of any density, viscosity or consistency that allows a user, depending on his or her abilities and limitations, to withdraw or "suck" the beverage though a conventional drinking straw. Beverage is also meant to include liquid pharmaceutical formulations for treatment of illnesses or diseases that are intended for oral delivery.

The term "nutrients" as used herein, broadly includes any chemical component of the beverage that has dietary or nutritional importance to the user. For example, nutrients may include essential nutrients such as proteins, fats, carbohydrates, minerals, and vitamins, as well as non-essential nutrients such as dietary fiber and cholesterol. For purposes of the present specification, the terms "nutrient" or "nutrients" are also intended to include all other constituents in the liquid or beverage being consumed by the user, such as caffeine, pharmaceutical ingredients, and water.

A "Portable Beverage Dispenser" ("dispenser") is defined as the apparatus of the present invention, in its various embodiments without limitation, that allows a user the ability to automatically monitor and control a user's intake of calories, nutrients, caffeine, or other constituents of the beverage being consumed.

A "drink experience" or Drink Duration ("DD") is defined as the duration between the time that a user chooses to take a first sip of a chosen beverage and the time that the user or dispenser completes or terminates consumption of that beverage.

A "sip" is defined as a small mouthful of liquid or beverage consumed by a user.

A "Sip Volume" ("SV") is defined as the volume of liquid that a person ingests in a sip. Researchers have found that sip volumes (minimum, normal, and maximum) vary depending on a person's age, sex, and weight. The Sip Volume can be determined by the microprocessor or an external data processor or can be specified by the user.

A "Sip Duration ("SD")" is defined as the duration between the time that a user initiates the sip and time that the sip is terminated.

The "Sip Interval ("SI")" is defined as the time interval or duration between any two successive sips within the Drink Duration. The Sip Interval can be determined by the microprocessor or an external data processor or can be specified by the user. The Sip Interval may be of equal duration between any two successive sips or the Sip Interval may vary between any two successive sips that comprise the Drink Duration.

The "Sip Rate ("SR")" is defined as the rate, for example, in milliliters per second, at which the liquid or beverage is transferred from the dispenser to the user for consumption. The Sip Rate is related to several parameters including but not limited to cross-sectional or radial area of the drinking straw or other conduit that carries the liquid, density of the liquid, internal resistance to flow within the drinking straw or other conduit, level of liquid in the container, and suction force applied by the user sucking on the straw. The Sip Rate can be specified by the user or can be determined by the dispenser, and is governed by Bernoulli's principle of hydrodynamics.

Referring to FIGS. 1 and 4-7, the first embodiment of the present invention includes a Dispenser 1 for monitoring and controlling a user's consumption of a chosen beverage. Dispenser 1 comprises a core liquid container ("container") for holding the beverage, a drinking straw 3 ("straw") or mouthpiece 4 through which the beverage is transferred from the container 2 to the user for consumption, a base component 5 ("base") attached to the bottom of the container 2, and a lid assembly ("lid") 6. The base 5 can be attached to the bottom or closed end (end opposite the open end that attaches to lid 6) of the container 2 by a threaded connection, a press-fit connection, or by any other suitable method of connection known to those skilled in the art. The base 5 is fabricated from a material, for example a rubber that is suitable for the service, which provides impact dampening in the event, for example, the container 2 or fully assembled Dispenser 1 is inadvertently dropped. The rubber can be chosen from any of one or more natural or synthetic rubbers. In addition to impact dampening, the base 5 can be fabricated from one or more materials that have heat transfer properties that are conducive to minimizing heat loss to assist in maintaining the beverage in the container 2 in a hot or cold state. Lid 6 can comprise an outer layer of material suitable for absorption of impact, for example a rubber that is suitable for the service, such as described previously. For example, if the Dispenser 1 were to be dropped from a typical adult standing height, the outer layer surrounding the lid assembly would dampen or lessen the force of impact acting against components internal to the lid 6. Embodiments of the present invention allow the user to readily interchange straw 3 with mouthpiece 4, without loss of functionality (see FIGS. 1A and 1B).

Referring to FIGS. 6A-B, in the first embodiment of the invention, straw 3 is fabricated as one continuous member with no internal obstructions, having an appearance similar to that of a conventional or standard drinking straw. The straw 3 extends from the user's mouth or proximal end of the straw, through a connection port 16 and extending partially into lid 6, through a flexible conduit ("sleeve") 22 internal to the lid 6, so that the distal end of the straw 3 is located near or at the bottom end of the container 2. Within lid 6, connection port 16 and outlet port 17 serve to support and align the straw though lid 6. In the case of operation with a straw 3 (FIG. 6A), tube 18 can be used to provide added support to straw 3 and can be utilized in controlling liquid flow, as described later (FIG. 8). In the case of operation with a mouthpiece 4 (FIG. 6B), tube 18 is not required and is omitted by the user. Although the straw 3 shown in the drawings has a circular shape in the axial direction, the straw 3 can have any other axial shape, for example oval or hexagonal, and can have any shape in the longitudinal direction, for example a curved or "crazy straw" configuration, provided the portion of the straw that is within lid 6 is straight in the longitudinal direction and can fit within sleeve 22. Straw 3 is preferred to be a reusable straw fabricated of a flexible or non-rigid food-grade rubber or rubber/plastic composite. Alternatively, standard flexible or non-rigid disposable straws can be used that are fabricated of other materials including but not limited to rubber, plastic, or paper. A rigid or non-flexible reusable or disposable straw may also be used where constriction of straw 3 is not required to control sip rate, such as when only LRV 26 (FIG. 8A) is utilized to control liquid flow.

When using straw 3, the user holds dispenser 1 in a vertical or slightly tilted position while sucking on the exposed proximal end of straw 3, as would be done when using a conventional straw and beverage container. When using straw 3, the liquid is withdrawn from the bottom of the container 2, through the distal end of straw 3, by suction force applied by the user at the proximal end of straw 3. Straw 3 can be inserted through a tube 18 that extends from the bottom portion of lid 6 to the bottom end of container 2.

In the case of operation without a straw, such as may be required by small children or medical patients that are unable to suck liquid through a straw, mouthpiece 4 (FIG. 1B) can be interchanged for straw 3. In the first embodiment of the invention, mouthpiece 4 is fully open at both opposing ends with no internal obstructions. Mouthpiece 4 can be attached to connection port 16 by a threaded connection, a press-fit connection, or by any other suitable method of connection known to those skilled in the art. The user withdraws liquid from the top end of the container 2, with outer tube 18 removed, by tilting dispenser 1 until liquid is allowed to enter outlet port 17 via gravity and flow through sleeve 22 to the user for consumption through mouthpiece 4. This operation is also similar to a conventional mouthpiece.

Container 2 is fabricated of a material such as a food-grade plastic, that may include but is not limited to polyethylene terephthalate ("PET") and high density polyethylene ("HDPE"). A graduated scale 11 can be imprinted on the outer surface of container 2 to indicate volume of liquid, for example milliliters or fluid ounces, corresponding to a location along the longitudinal axis of container 2.

Figure 7:
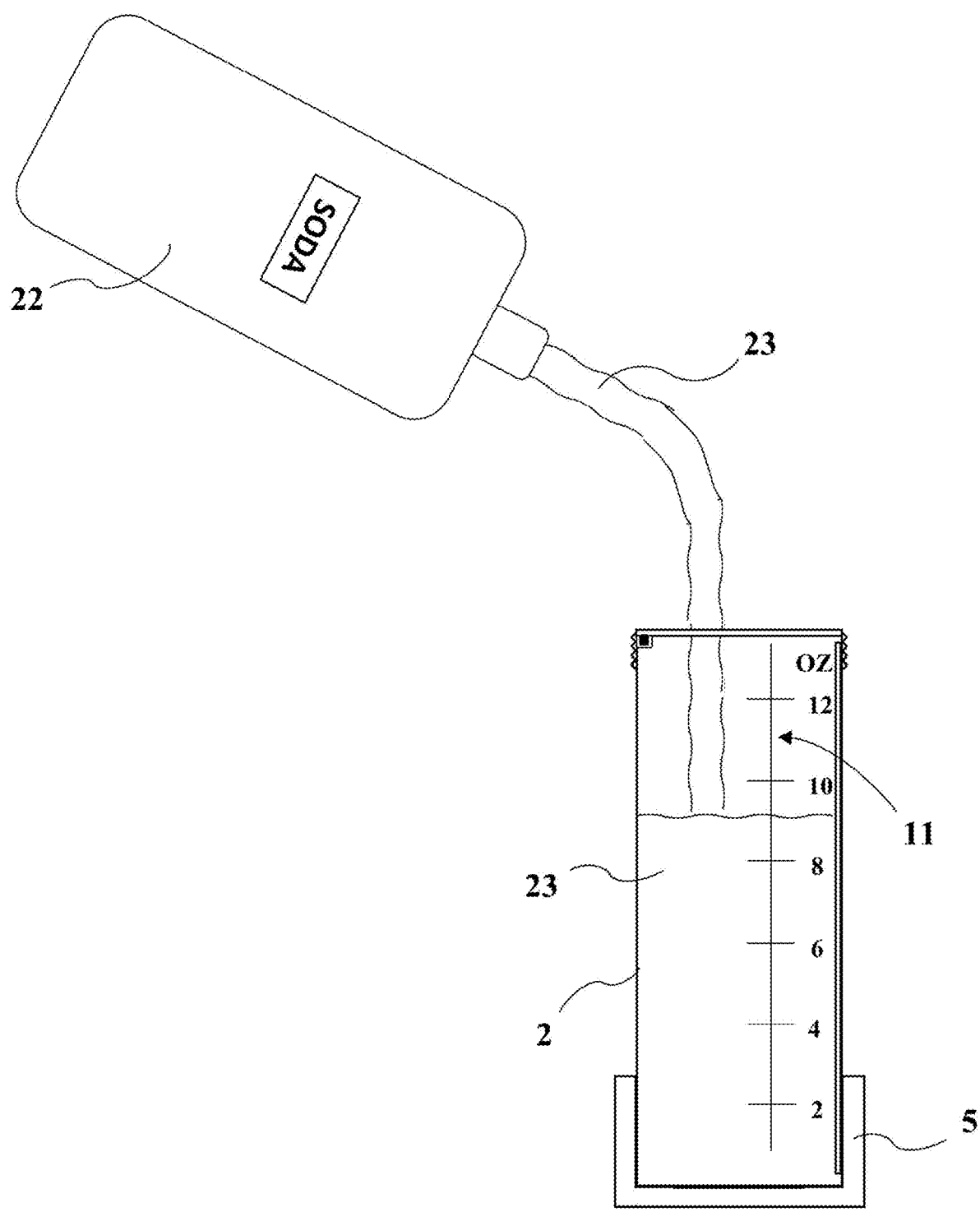
FIG. 7 is an elevation view of a first embodiment of the present invention indicating fill method (pouring, use of gravity)

Referring to FIG. 7, in the first and alternate embodiments of the invention filling of container 2 with beverage 23 can be accomplished without requiring an internal or external pressure inducing device, such as a pump. For example, prior to installing lid assembly 6, container 2 can be filled by pouring the user's preferred beverage 23 from an external container 22, for example a two liter bottle of soda, directly into container 2 until the desired volume of liquid is reached as indicated on the imprinted graduated scale 11. Referring to FIG. 8, upon completion of filling container 2, the top portions of tube 41 and tube 18, that are contained within lid 6, are joined at joint 109 by threaded coupling or other suitable connection method known to those skilled in the art. The external container 22 can be any container or device that allows filling of container 2 with beverage 23, by use of gravity or other suitable means (for example an automatic liquid dispenser). Electronic components within the lid 6 communicate with one or more external devices, for example Personal Computer (not shown) ("PC", intended to include both WINDOWS® and MAC® computers) (WINDOWS® and MAC® are registered trademarks of Microsoft Corp, Redmond, Wash. and Apple, Inc., Cupertino, Calif., respectively) or laptop computer 9 or wireless portable devices 10 such as smart phones, and tablet devices. Communication with these devices can occur through either a wired connection 7 (such as Universal Serial Bus (("USB")), IEEE1364 ("Firewire"), or THUNDERBOLT (Registered trademark of Apple, Inc. Cupertino Calif.) or other form of wired communication) or wireless connection 8 (WiFi, cellular data, infrared, or other form of wireless communication). The lid 6 can receive settings and instructions from the user via an external device 9 or 10 to initiate and control a drink experience. The connection port 13 on the external portion of the lid assembly 6, or other suitable connection port, provides power for a rechargeable battery (28, FIG. 8A), that can be supplied from a suitable electronic device, for example a PC or laptop computer 9, or from other external power source, for example a wall outlet 15 through a power adapter 14.

Referring to FIGS. 8-9, in the first embodiment of the present invention, lid assembly 6 contains two liquid regulating valves ("LRV") 25 and LRV 26 that can control the user's drink behavior of beverage 23 delivered to the user by dispenser 1, either through a straw 3 (FIGS. 8A-G) or a mouthpiece 4 (FIGS. 9A-D). In addition to LRV 25 and LRV 26, lid assembly 6 includes a flexible conduit or sleeve 22, back plate 34, and electronics that may include but are not limited to: microprocessor 27, rechargeable battery 28, switch 36, push buttons, sensors, light emitting diodes ("LEDs"), and other electronics as required for operation of dispenser 1. Alternatively, any or all of the electronics, including microprocessor 27, can be located in base 5 or other suitable portion of dispenser 1. In one embodiment of the invention, the processing of information, for example the determination of Sip Intervals and Sip Volume is performed by microprocessor 27 and/or by software or application ("App") stored on the user's wireless device and/or by an external data processor. Microprocessor 27 enables control of input and output devices and signals, and can perform certain calculations such as determining when and how to actuate LRV 25 or LRV 26 based on liquid level in container 2. In other cases, microprocessor 27 can be substituted with a microcontroller or other processing device, to best suit the intended use and system configuration.

In the case of operation with straw 3, one or more concentric sleeves 22 fully encompass a portion of straw 3 within lid assembly 6 to prevent leakage of liquid into the inner compartment of lid assembly 6 in the event straw 3 is damaged and leaking, which could damage LRV 25 and 26, electronics, and other components.

Figure 8A:
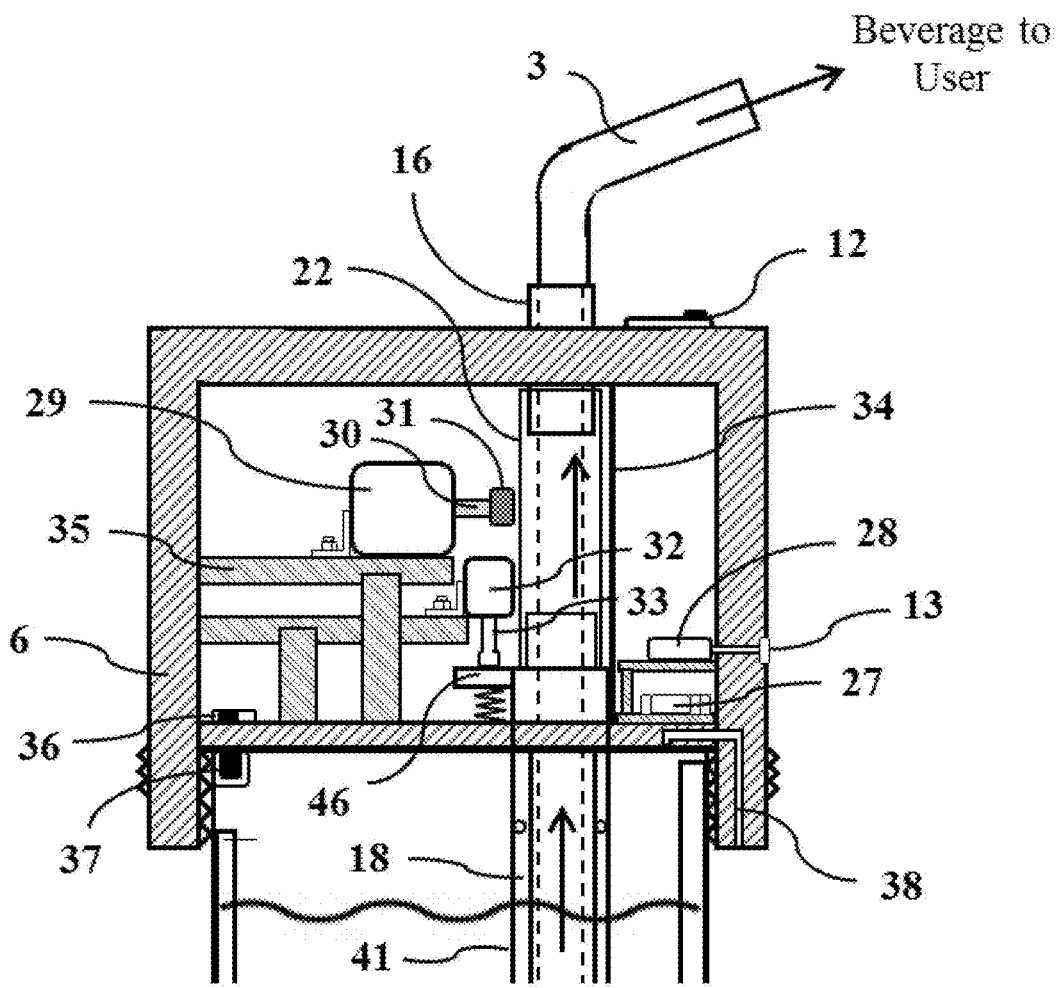
FIG. 8A is a cut-away elevation view of a first embodiment of the invention, employing a straw and two liquid regulating valves; arrows indicate the direction of flow of liquid in the dispenser.

In the case of operation with mouthpiece 4 instead of straw 3, the innermost sleeve 22 becomes the means by which fluid or beverage 23 is transferred from container 2 to the user. The preferred cross-sectional (direction perpendicular to fluid motion) shape of sleeve 22 is hexagonal due to optimal closure tightness and control features. Alternatively, sleeve 22 can have a cross-sectional shape that is rectangular, round, oval, or other shape that satisfies the intended purpose. Referring to FIGS. 8A-B, LRV 25 comprises a linear actuator motor 29 that drives bar 30 that is attached to plate 31. Motor 29 rotates a specific number of turns or steps corresponding to the desired linear travel of bar 30 and plate 31. Motor 29 can be a stepper type motor (for example Haydon Kerk 15000 Series Linear Stepper Motor). Other motors can also be employed such as a servo motor, DC motor, or other motor known to those skilled in the art that can be configured to provide linear motion. For example, a DC motor can be attached to an external gear set such as a rack and pinion. As plate 31 moves linearly toward sleeve 22, the plate 31 applies a linear force against the exterior surface of sleeve 22, causing straw 3 and sleeve 22 to constrict. Back plate 34 provides a resistive force against plate 31 to allow straw 3 and sleeve 22 to be compressed.

LRV 26 comprises a motor 32 similar to that of LRV 25, but can be of a different type and size than motor 29. Motor 32 rotates a specific number of turns or steps corresponding to the desired linear travel of bar 33. A spring 42 exerts a continuous force against top lip 46. Bar 33 travels linearly towards top lip 46, exerting a force exceeding the force being applied by spring 42 such that tube 41 moves linearly away from motor 32. Tube 41 is allowed to slide with minimal resistance against tube 18 employing O-ring 43 or other means known to those skilled in the art, such as ball bearings. Distal end 48 of tube 18 is open to allow liquid to enter straw 3 through tube 18.

A "full open" position is the position of LRV 25 and/or LRV 26 that enables the transfer of liquid from container 2 to the user for consumption at the maximum Sip Rate. A "full closed" position is the position of LRV 25 and/or LRV 26 that prevents any transfer of liquid from container 2 to the user for consumption (Sip Rate=0). A "partial open" position is the position of LRV 25 and/or LRV 26 that enables the transfer of liquid from container 2 to the user for consumption at an intermediate Sip Rate, for example at 25% or 50% of the maximum Sip Rate. The Sip Rate can be set by the user, determined by microprocessor 27, or determined by an external processor such as an App stored on user's wireless device.

The Sip Rate can be related to reference data and user profile settings, such as age and medical limitations, healthy drink behavior, historical performance (as recorded by the dispenser), dietary goals such as limits on nutrient consumption, hydration goals, personal preferences, and/or physical limitations of the dispenser as dictated by Bernoulli's principle of hydrodynamics. The Sip Rate is also dependent on the magnitude of the suction force that the user applies at the proximal end of straw 3 when consuming beverage 23. For operation with LRV 25, the Sip Rate is related to the percent open area of the straw 3 (operation with straw) or sleeve 22 (operation with mouthpiece) due to constriction of straw 3 or sleeve 22.

The "percent open area" is defined as the cross-sectional area (in the axial direction) of straw 3 or sleeve 22 in the partially constricted state divided by the full cross-sectional area of straw 3 or sleeve 22 in the unconstricted state, multiplied by one hundred. For example, for straw 3, the formula for percent open area is:

$$\% \text{ open area} = \frac{\text{(cross-sectional area of partially constricted straw 3)}}{\text{(full cross-sectional area of unconstricted straw 3)}} \times 100$$

The percent open area can be related to the Sip Rate either empirically or mathematically by employing Bernoulli's laws of hydrodynamics. For example, to provide a Sip Rate that is 50% of the maximum Sip Rate, it may be required to constrict straw 3 to an open area of 60%. The maximum Sip Rate is primarily governed by the unconstricted cross-sectional area of the straw or mouthpiece and the amount of suction force that the user is able to apply at the proximal end of straw 3 or degree of inclination of the dispenser (for operation with mouthpiece 4).

LRV 25 or LRV 26 can be used alone or in any combination to provide control of all drink parameters. Referring to FIGS. 8A-G, in one possible combination LRV 25 is utilized mainly to control Sip Rate, while LRV 26 controls drink parameters such as Drink Duration, Sip Duration, Sip Intervals, and Sip Volume. FIGS. 9A-E shows another possible combination where LRV 26 is omitted and LRV 25 controls all drink parameters including Drink Duration, Sip Duration, Sip Intervals, Sip Volume, and Sip Rate. Any combination of LRV 25, LRV 26, straw 3, and mouthpiece 4 can be employed.

Figure 8C:
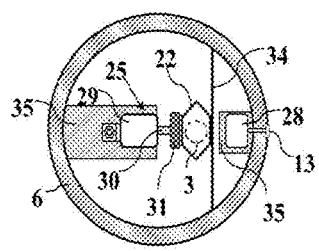
FIG. 8B-G are cut-away elevation and plan views of operation of the dispenser, employing a straw and two liquid regulating valves; arrows indicate the direction of flow of liquid in the dispenser.
Figure 8E:
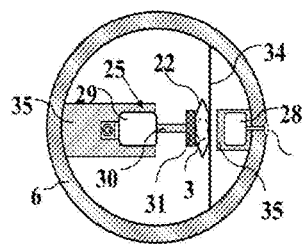
Figure 8G:
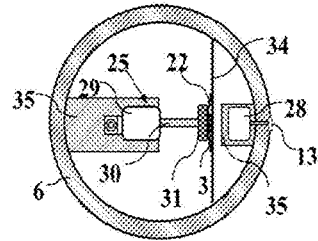
Figure 8B:
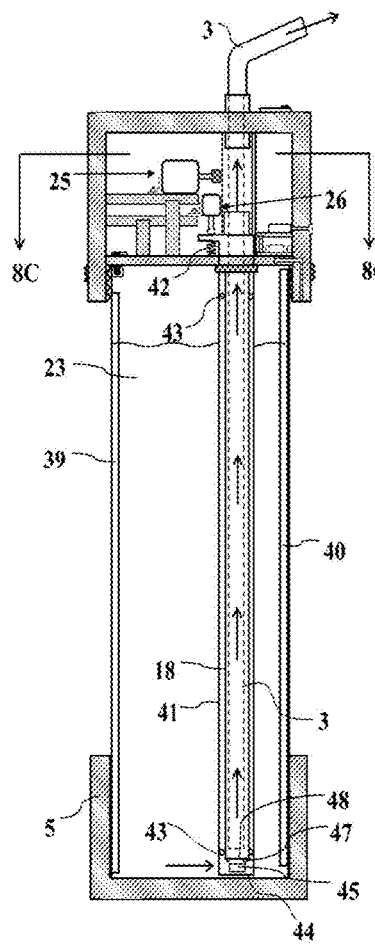

Referring to FIGS. 8B-C, LRV 25 is placed in a full open position by retracting plate 30 away from back plate 34 such that it does not provide a linear force against sleeve 22, thereby allowing sleeve 22 and straw 3 (if inserted) to provide a 100% open area, thereby producing a maximum Sip Rate. Referring to FIGS. 8F-G, LRV 25 is placed in a full closed position by extending or moving plate 30 toward back plate 34 until it provides enough linear force against sleeve 22 to cause a full constriction (0% open area) of sleeve 22 and straw 3 (if inserted), thereby preventing any liquid from being transferred from container 2 to the user for consumption.

Figure 8D:
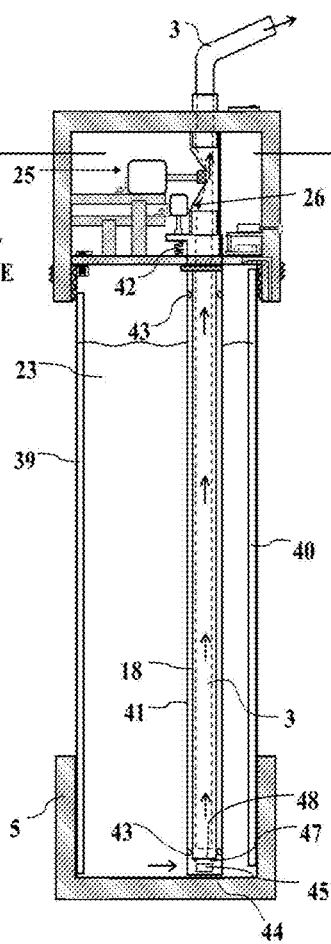
Figure 8F:
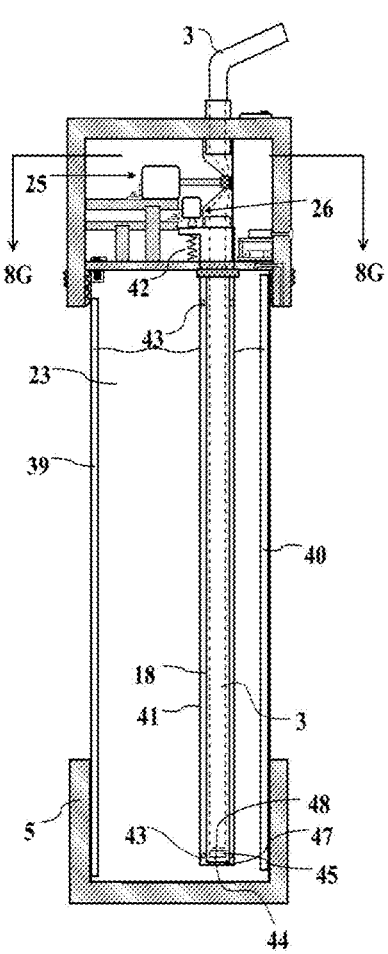

Referring to FIGS. 8D-E, LRV 25 is placed in a partially open position by extending or moving plate 30 toward back plate 34 until there is sufficient linear force against sleeve 22 to cause a partial constriction (for example 25% or 50% open area) of sleeve 22 and straw 3 (if inserted), thereby producing a Sip Rate that is some fraction or percentage of the maximum Sip Rate. The distance travelled by bar 30 and plate 31 is controlled by microprocessor 27 based on the required percent open area of straw 3 or sleeve 22 that transmits the liquid.

Referring to FIGS. 8B-C, LRV 26 is in a full open position when bar 33 moves linearly toward top lip 46 of tube 41 and moves tube 41 linearly such that opening 45 at the distal end of tube 41 allows liquid to enter into straw 3 through tube 18. Referring to FIGS. 8F-G, LRV 26 is in a full closed position when bar 33 moves linearly away from top lip 46 of tube 41 such that bottom surface 44, which has a solid surface, of tube 41 presses firmly against the bottom portion of tube 18, that can include O-ring 47, preventing liquid from entering opening 45 and straw 3. Spring 42 continuously exerts a compressive force against top lip 46 causing bottom surface 44 of tube 41 to press firmly against bottom portion of tube 18. In the case where LRV 25 is omitted and LRV 26 is used to control all drink parameters, LRV 26 can be placed in a partial open position (not shown) by moving tube 41 linearly such that only a portion of opening 45 allows liquid to enter straw 3.

Referring to FIGS. 8-9, liquid level sensor 40 is shown as a capacitive or resistive type sensor to measure the level of liquid in container 2. Sensor 40 can be located anywhere within Dispenser 1 that satisfies the functional requirements of sensor 40. The level of liquid that is in container 2 can be measured using any liquid level measurement device and sensor, employing capacitive, resistive, ultrasonic, optical, or other methods that are known to those skilled in the art. The Sip Volume to be dispensed to the user is controlled by LRV 25 or LRV 26 by measuring a change in liquid level during the Sip Duration, as continuously measured by sensor 40, which is mathematically proportionate to the Sip Volume to be consumed by the user. For example, if container 2 is a straight cylindrical vessel, then the Sip Volume consumed is equal to the cross-sectional area of the cylinder in the axial direction multiplied by the change in level of the liquid during the Sip Duration. For an irregularly shaped liquid container, a correlation between change in liquid volume and change in liquid level can be determined empirically.

Referring to FIGS. 8A-B, this first embodiment of the present invention includes a temperature sensor 39 that can be attached to an internal portion of container 2 to measure the temperature of beverage 23 that is in container 2 at any time. The temperature is continuously read by microprocessor 27. Temperature sensor 39 can be a thermocouple type, but other commonly available types of temperature sensors can be used. The microprocessor 27 can alert the user or take corrective action, for example terminate the drink experience, if temperature of beverage 23 exceeds or drops below limits set by the user or as determined by the microprocessor 27 or external data processor. Channel 38 provides a means for releasing or venting to atmosphere any air or vapor, for example carbon dioxide released by carbonated beverages, that is present above the liquid level of beverage 23 within container 2. Lattice 35 serves to provide structural support for LRV 25 and LRV 26. Any means known to those skilled in the art can be employed to prevent LRV 25 and LRV 26 from moving or dislocating while lid 6 is in motion or experiences external force or shock, such as when dispenser 1 is inadvertently dropped.

Figure 13A:
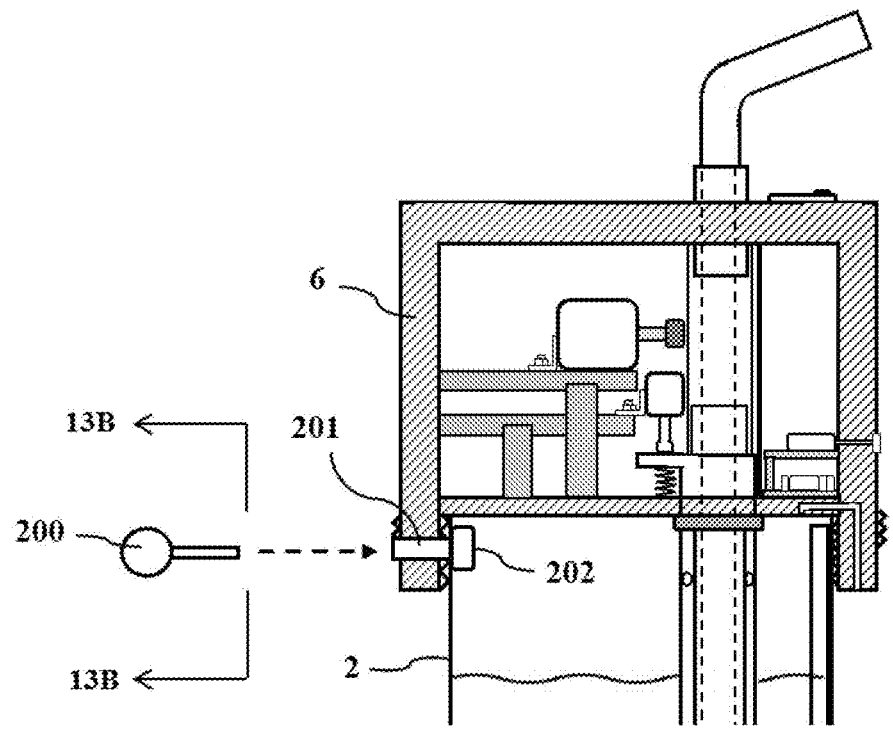
FIG. 13A is an elevation view of the dispenser depicting a mechanism for manually locking the lid assembly.
Figure 13B:
FIG. 13B is an end view of the user-specific key design.

A mechanical key (FIGS. 13A-B) or locking mechanism can be used to prevent a user from manually detaching lid 6 from container 2. The locking mechanism is intended for use by a care-giver to prevent a user from accessing the contents of the dispenser, and can also be used to protect against accidental opening of the lid 6 during use, transport or storage. Key 200, key guide 201 and key base 202 can be any conventional key assembly type, for example a barrel or cam type assembly. Key 200 can have a user-specific key combination design as shown in FIG. 13B (for example). A drink experience can be terminated at any time by the user, or by the microprocessor 27 if permission is granted by the user, for example when a specified limit for nutrient consumption, water or liquid volume, or maximum liquid temperature has been exceeded, when the maximum Drink Duration has transpired, or when the total volume of liquid or beverage is completely consumed. The drink experience can also be terminated by the microprocessor 27 if the power level of the battery drops below a specified minimum value, for example 10%. The user can select, for example when creating the user profile, whether LRV 25 and/or LRV 26 is to be placed in a full-open ("fail open") or full-closed ("fail closed") position during a low power occurrence or if any malfunction were to occur. If "fail open" is chosen, the user will be allowed to drink freely, as with a conventional unobstructed drinking straw or mouthpiece. If "fail closed" is chosen, the user will not be able to drink any remaining beverage.

Referring to FIG. 8A, a switch 36 is attached to an interior section of lid assembly 6 such that when it aligns with and is in close proximity to a magnet 37 attached to interior portion of container 2, switch 36 forms a closed circuit and immediately signals to the microprocessor 27 that lid assembly 6 is in the closed position, as indicated by illumination of LED 19 on user interface 12 (FIG. 5E) and/or as notified to user through user's wireless device, employing a visual, audible, or other such commonly employed notification method. Switch 36 may be magnetic type, such as a reed switch, a direct contact switch, or other switch known to those skilled in the art. The activation of switch 36 signals to microprocessor 27 that the user has completed filling Dispenser 1 with the chosen type and amount of beverage 23, that lid 6 has been securely attached to container 2, and that Dispenser 1 is ready to begin dispensing beverage 23 to the user based on the drink parameters established by the user, and/or microprocessor 27, and/or or an external data processor such as an App installed on user's wireless device. These drink parameters normally include Sip Interval, Sip Duration, Sip Volume, Sip Rate, and Drink Duration, but can include other drink parameters based on the intended application or use of the dispenser. The user may choose to drink a plurality of sips during each "Sip Duration". In this case, the microprocessor 27 calculates the "total" Sip Volume as the Sip Volume per sip multiplied by the number of sips per Sip Duration. Upon activation of switch 36, microprocessor 27 places LRV 25 and/or LRV 26 in a fully open position or partially open position as determined by the microprocessor or external data processor, records the total "starting" volume and liquid level (L0) of beverage 23 stored in container 2, and illuminates LED 20 on user interface 12 and/or through an App installed on user's wireless device, to signal to the user that a sip of beverage 23 is ready to be taken. At this time, the user can choose to initiate a sip of beverage 23 by pressing "start" button 21 on user interface 12, enable the sip by controls on the user's wireless device, or the user can start to take a sip through straw 3 or mouthpiece 4. The microprocessor 27 detects that the user has begun to take a sip by sensing a change in liquid level based on input signal from sensor 40. It is to be understood that depressing button 21 is not required to initiate a sip, since sensor 40 provides confirmation to microprocessor 27 that the user has begun a sip. Based on the required Sip Volume for the current sip, which is equivalent to the change in liquid volume in container 2 during a sip, microprocessor 27 calculates the required change in liquid level (DL) by the methods discussed earlier, such as obtaining an empirical relationship between the volume of container 2 and liquid level in container 2. The microprocessor 27 then calculates the "ending" liquid level (L1) by the formula:

$$L1 = L0 - DL$$

Figure 9B:
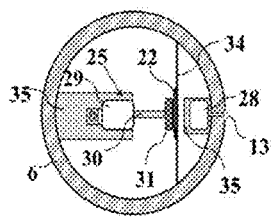
FIG. 9A-D are cut-away elevation and plan views of operation of the dispenser, employing a mouthpiece and one liquid regulating valve; arrows indicate the direction of flow of liquid in the dispenser.
Figure 9D:
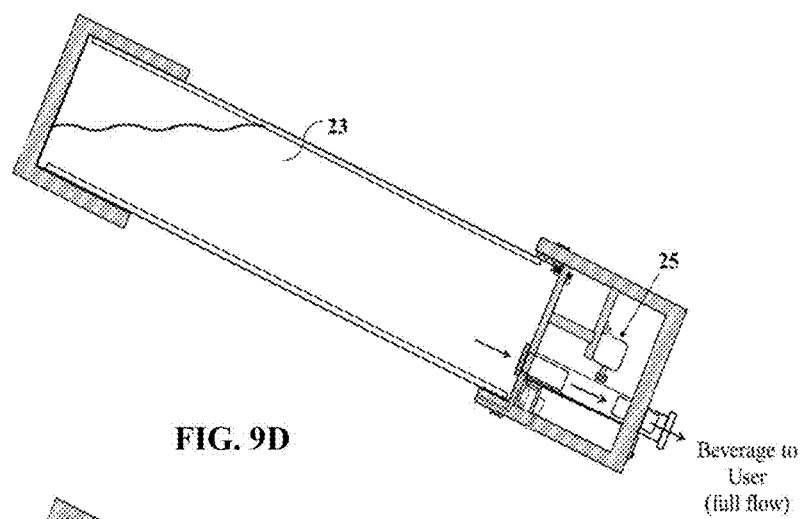
Figure 9A:
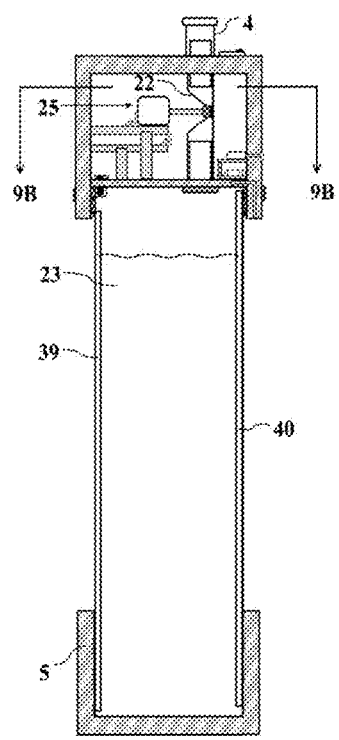
Figure 9C:
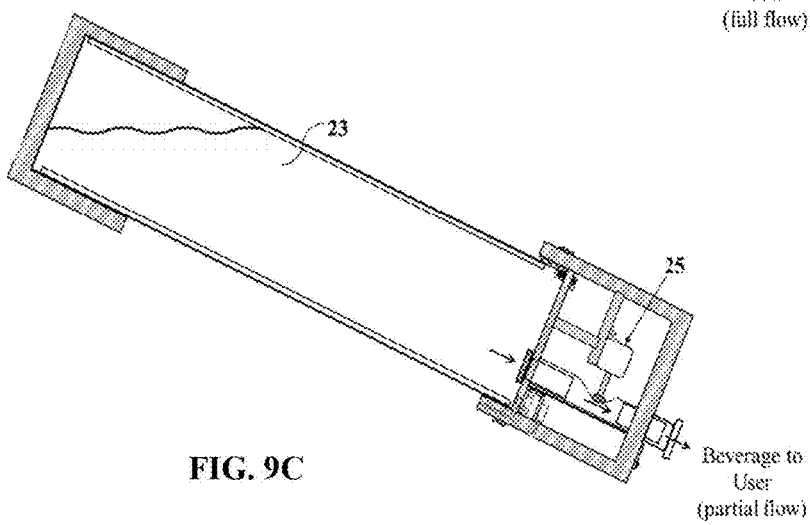

When the liquid level in container 2 reaches liquid level L1, microprocessor 27 places LRV 25 and/or LRV 26 in the fully closed position. The microprocessor 27 can account for the "lag time" associated with closing LRV 25 and/or LRV 26, by sending the signal to fully close LRV 25 and/or LRV 26 at a specified time prior to reaching liquid level L1. The specified time can be determined based on the Sip Rate during the current sip. The Sip Rate (for example, milliliters per second) can be estimated as the change in liquid volume divided by time elapsed during the current sip. Since Sip Rate can vary based on suction force applied by the user, which can be arbitrarily altered by the user, an adaptive control method can be employed to provide better estimates for the Sip Rate. A least squares method can be employed as an estimating method. After LRV 25 and/or LRV 26 are in the fully closed position, microprocessor 27 initiates a Sip Interval time counter in preparation for the next sip and notifies the user that a sip is not permitted, such as by ceasing the illumination of LED 20 or changing the color of LED 20 from green to red, for example. The Sip Interval or time between successive sips, is normally determined by microprocessor 27 or by an external data processor, or it can be set by the user. When the Sip Interval has elapsed, and accounting for lag time, microprocessor 27 places LRV 25 and/or LRV 26 in the fully open position or partial open position and illuminates LED 20 indicating to the user that the user may take his or her next sip of beverage 23. The microprocessor 27 then repeats the steps previously described to control the current sip. The same sequence of steps is followed for all successive sips until the entire volume of beverage 23 has been consumed by the user, or the user chooses to terminate the drink. Alternatively, the user can choose to have microprocessor 27 or external data processor, such as App installed on a user's wireless device, terminate the drink experience. For example, the App on user's wireless device may terminate the drink experience or may prevent the user from consuming any more of a specific beverage or plurality of beverages (from user's Beverage List) if the user has exceeded his or her daily liquid consumption limit for caffeine. In this case, the App would notify the user when another drink experience can be initiated for these beverages, or prevent consumption of those beverages until a specific time interval has elapsed, which can be estimated by the App based on long-term dietary goals and historical drink behavior. At the completion of the drink experience, microprocessor 27 can store and/or transmit information about the drink experience to an external data storage device such as "cloud computing" that can be accessed on a user's wireless device or PC. The information collected by the microprocessor 27 can include, for example, total consumption of a specific nutrient in comparison to limits (daily, weekly, etc.) specified for that nutrient, to aid in dietary control. The total consumption of water that was contained in beverage 23 can also be calculated and recorded for hydration requirements, by accounting for the density of the beverage being consumed. The density of each beverage can be included in the data included in the Customized Beverage List and Master Beverage List. Referring to FIGS. 9A-C, Dispenser 1 shows operation with mouthpiece 4 and LRV 25; LRV 26 can be utilized instead of LRV 25. The operation of this device is similar to that shown in FIGS. 8B-G, with the exception that an attitude sensor can be utilized to determine when the user initiates a sip and can correct for liquid level measurements determined through the use of sensor 40.

Figure 3:
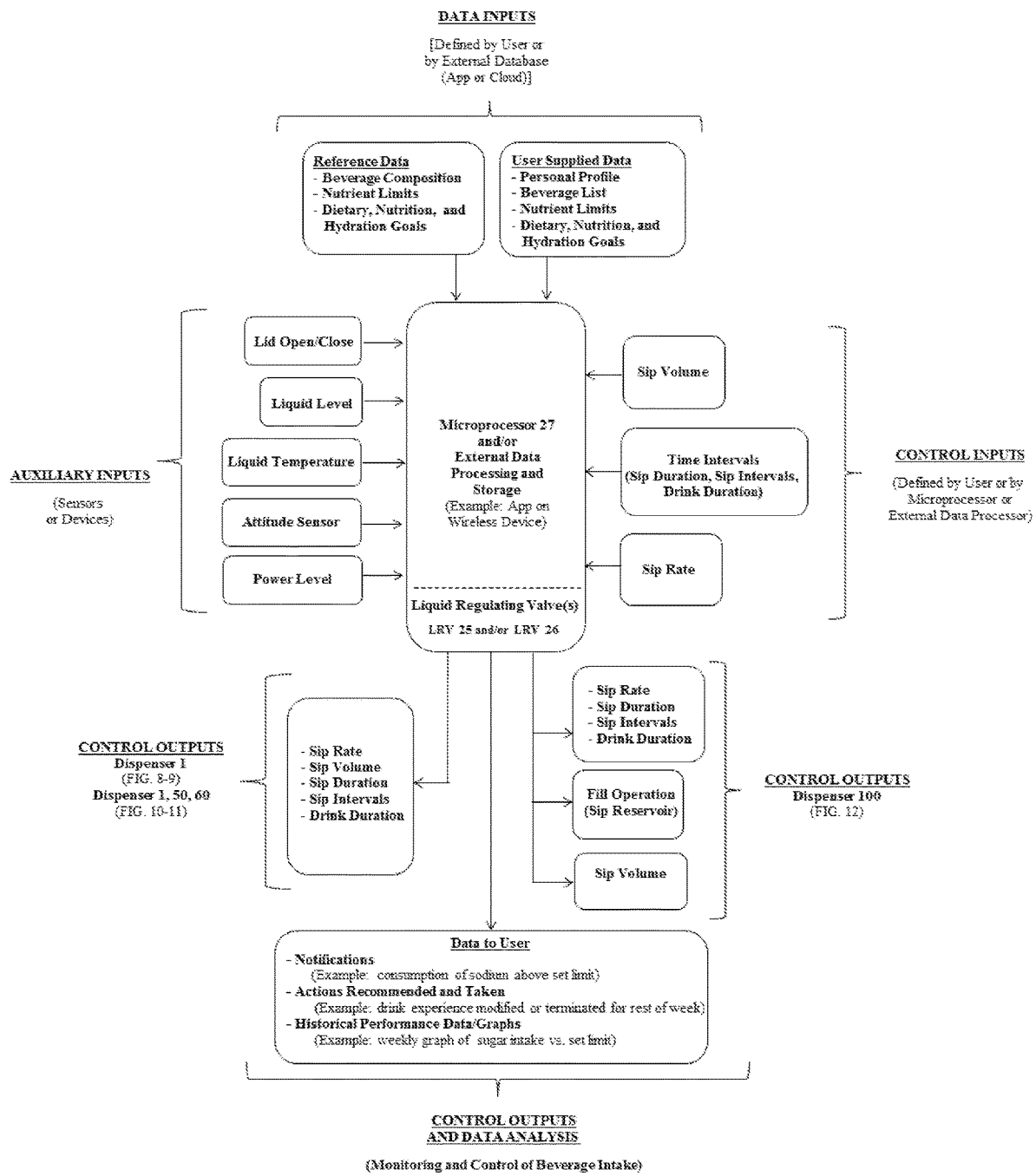
FIG. 3 illustrates the various input data and control parameters defined by the user and microprocessor or external data processor, employed to control beverage consumption.
Figure 4:
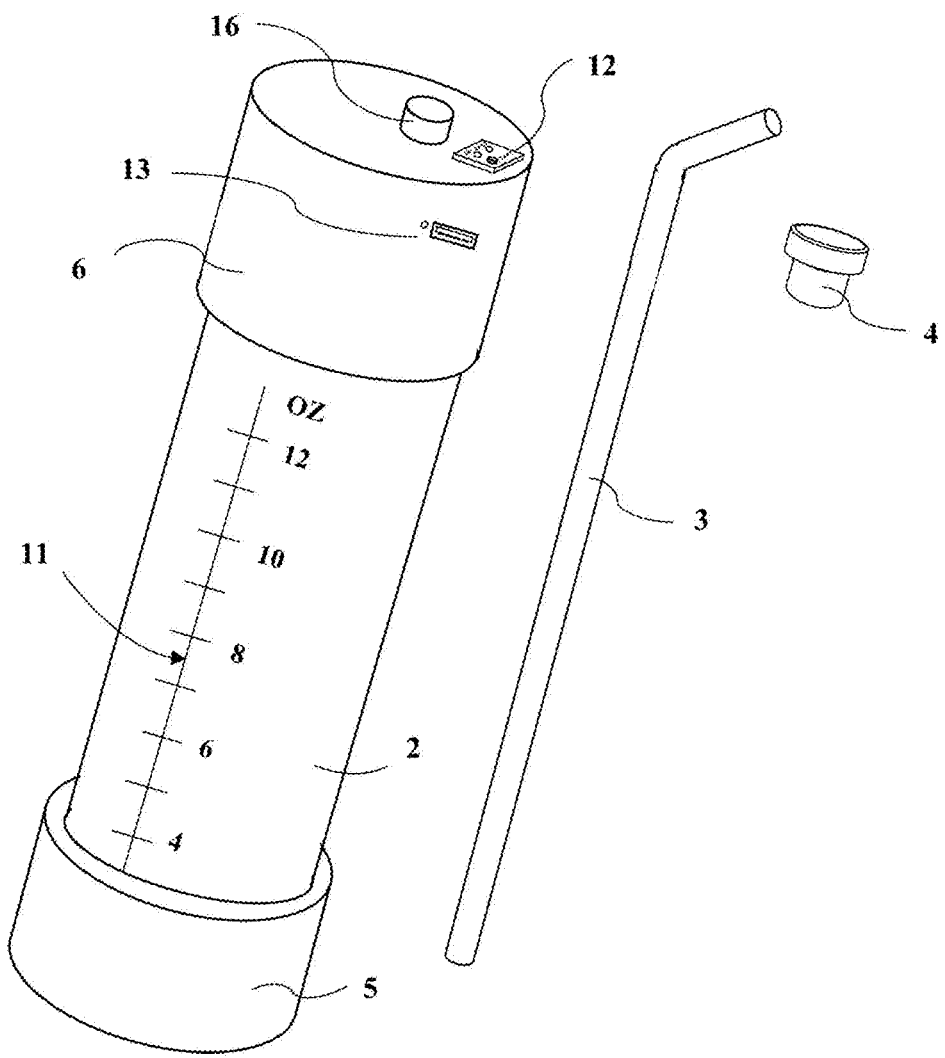
FIG. 4 is a perspective view of the embodiments shown in FIG. 1A and FIG. 1B, showing the straw and mouthpiece removed from the dispenser.
Figure 5B:
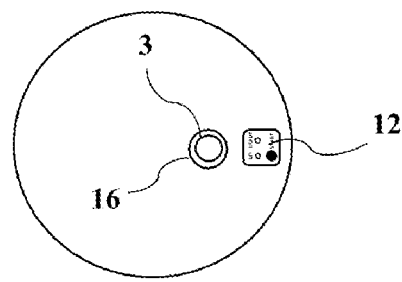
FIG. 5A-E are elevation and plan views of a first embodiment of the present invention.
Figure 5E:
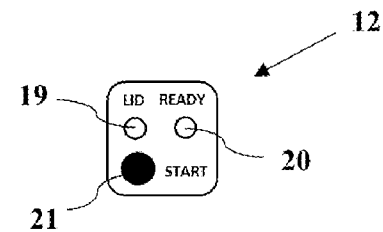
Figure 5A:
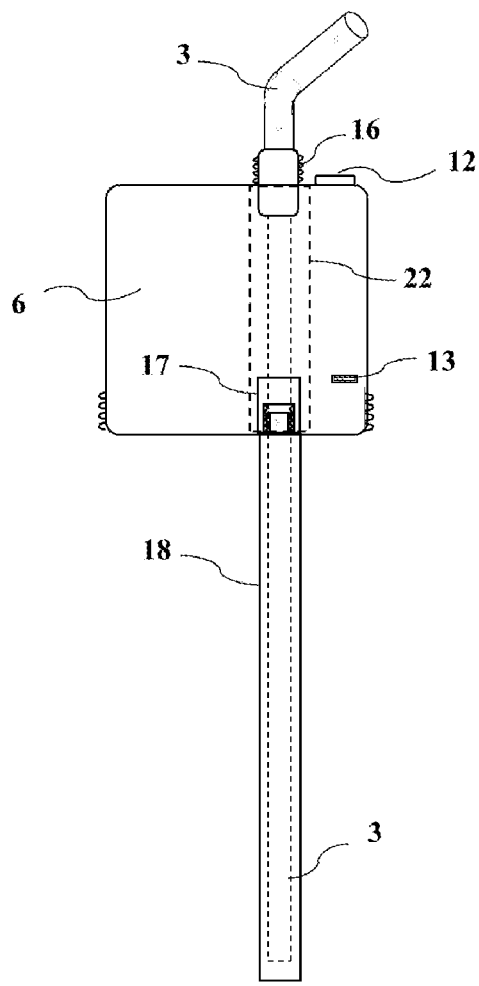
Figure 5D:
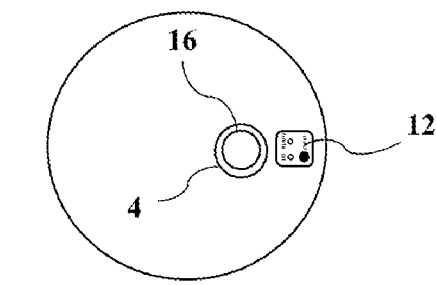
Figure 5C:
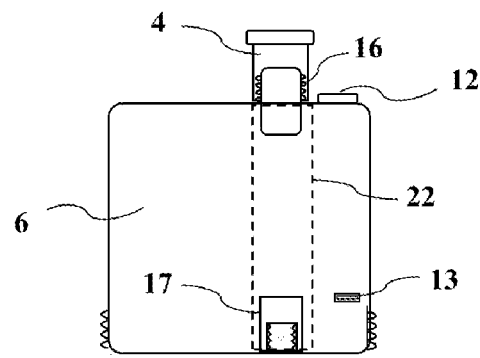

Referring to FIGS. 2 and 3, in the various embodiments of the present invention, the dispensers can be utilized for controlling liquid intake of water, nutrients, caffeine, sugar, and other constituents of a beverage 23 to be consumed by a user. Prior to initial use of the dispenser (as described in the various embodiments of the present invention), the user creates an electronic database of personal data related to the user's drink behavior, nutritional information based on user's custom list of beverages ("beverage list"), and dietary, nutritional, or medical/therapeutic goals. The user inputs data via a computer 9 or via an application ("App") on wireless device 10. The App can be provided by the manufacturer of the dispenser. All data submitted by user and data collected and produced by microprocessor 27 (FIG. 8A) is stored on external storage devices or on remote storage locations, for example cloud storage, except for the limited amount of data that is required for the operation of Dispenser 1, which data is stored within microprocessor 27.

In the first step of the setup process, a user creates a customized Beverage List consisting of beverages commonly consumed by one or a plurality of users, such that the customized Beverage List can be shared by a plurality of users in a household or medical facility, for example. In the case of medicinal treatments, for example, the beverages may be pharmaceutical formulations for treatment of illnesses or diseases. Each beverage is identified with a unique name, for example "Cola Soda 1". Alternatively, the user can select a beverage from a Master Beverage List that is provided by the manufacturer of the dispenser. The dispenser manufacturer can employ several methods to develop the Master Beverage List. For example, the dispenser manufacturer can obtain the nutrient content information from the websites of beverage manufacturers, federal or other public health organizations, research organizations, or other publicly available source of information. Nutritional information could also be obtained directly from a product manufacturer. The Master Beverage List can be stored on a remote data storage device or server, such as cloud storage, or for example it can be stored in an App that is installed on a user's wireless device. For each beverage, the user enters a reference serving size, for example 12 fluid ounces ("oz"), along with complete nutrient information corresponding to that serving size. The nutrient information, for example, the amount of sodium and sugars contained in a beverage, can be readily obtained from a "Nutrition Facts" table that is normally imprinted on a label affixed to a beverage container, for example a two liter bottle of orange flavored soda. The dispenser manufacturer can also provide optical recognition software that can be incorporated in the same App that the dispenser manufacturer utilizes to allow users to interface with and control the dispenser. A user can scan the information from the Nutrition Facts label imprinted on the beverage bottle and the optical recognition software can interpret the nutrient content information, and other pertinent information, and transfer the information to the Beverage List. Alternatively, the nutrition information for a specific beverage or type of beverage can be obtained from other methods or publicly available sources. Once the Beverage List has been created or updated, the user creates a personal profile, which the microprocessor 27 then associates with that user. The personal data can include any information specific to that user that may be pertinent in determining parameters that microprocessor 27 can use to control the operation of Dispenser 1. For example, microprocessor 27 can use equations or data "look-up" tables to determine Sip Volume, Sip Intervals, Sip Rate, and recommended daily intake of nutrients based on the user's age, sex, weight, geographic location, medical and physical limitations, and activity level. In the case of nutritional control, the personal data can include maximum limits or goals associated with chosen nutrients. For example, the user can set daily limits of 200 milligrams (mg) for sodium and 250 calories, from consumption of beverages or other liquids. The user can also set the percentage of calories and nutrients that is to be to be distributed to the consumption of liquids or beverages versus the consumption for food. For example, the user can set the total daily limit of calories from consumption of beverages to be 30% of the user's total calorie consumption (including food and beverages). Alternatively, microprocessor 27 can estimate, for example through the use of an equation or data tables, the recommended maximum daily nutrient limits based on personal data and published data on healthy nutritional intake. The recommended daily nutrient limits can be obtained from federal and governmental health organizations, medical journals or other scholarly publications, or other reliable and publicly available sources of information. The App that the manufacturer utilizes to allow users to interface with and control the dispenser can communicate with other "health" Apps that may have access to recommended nutrient consumption and other pertinent health related information. In a medical facility, for example, the dispenser manufacturer's App can interface and share data with that facility's databases and health related software applications. The total amount (for example as measured in milligrams) of a specific nutrient that a user consumes by ingesting a specific beverage can be calculated by multiplying the nutrient content per serving size by the amount, for example Sip Volume, of the beverage consumed by the user. For example, if a user consumed 50 ml (milliliters) of a cola soda that contained 30 mg (milligrams) of caffeine per 300 ml serving, then the amount of caffeine consumed by the user would be 5 mg (30 mg/300 ml*50 ml). Similarly, the amount of water contained in the amount of beverage consumed by the user can be calculated by correcting for the density of the beverage with density of water. In this fashion, the App supplied by the dispenser manufacturer can record the amount of each nutrient that the user consumes during each sip and for the entire drink experience. The microprocessor 27 measures the volume of beverage consumed as explained in describing FIGS. 8-9. The dispenser manufacturer's App can compare, on a continuous or periodic basis, the amount of a specific nutrient consumed by the user to the maximum daily limit set for that nutrient. Similarly, the dispenser manufacturer's App can compare the amount of a specific nutrient, for example calcium or Vitamin A, that a user consumed while drinking a beverage with the recommended daily intake for that nutrient. In this case, the recommended daily intake is a "goal" for the user to achieve instead of a limit to avoid. The dispenser manufacturer's App can record all nutrients consumed by the user for a specific beverage or any grouping of beverages during any period of time, for example daily or monthly, and make that information available to the user from the dispenser manufacturer's App or though databases stored on remote storage areas. The information can be made available to the user in the form of histograms or charts that can indicate when the user met or missed his or her recommended intake of nutrients, including consumption of the water component of each beverage.

During the setup process or during the drink experience, the dispenser can provide the user the option of allowing the dispenser to determine the appropriate action to take if one or more of the Nutrient limits has or is about to be exceeded. If the user allows the dispenser to take action, the dispenser may choose to terminate the drink experience and/or modify the drink experience. For example, if the maximum limit set for total daily calories is about to be exceeded, the dispenser can terminate the drink experience by placing LRV 25 and/or LRV 26 to full closed position. Alternatively, the dispenser can provide the user the option of completing the current beverage, but recommending that the current beverage not be consumed again for another two days, for example, to allow the user to meet the weekly limit for calories.

Referring to FIGS. 10A-B, in an alternate embodiment of the present invention, Dispenser 1 is surrounded by a second Dispenser 49 to form a single dispensing assembly ("Combined Dispenser 50"), such that Dispenser 1 functions as described previously with FIGS. 1-9 to control the frequency, duration, and rate of flow of a user's intake of beverage 23, while Dispenser 49 functions only to monitor the consumption of beverage 52. Beverage 24 and beverage 52 could be the same beverage, although they may be different beverages, for example, beverage 23 may be a cola soda and beverage 52 may be water. One use is when a parent may wish to control the nutritional intake that a child (user) obtains from consuming a sugary drink (beverage 23) via Dispenser 1, but only monitor the amount of water (beverage 52) that the child consumes from second Dispenser 49. By use of this alternate embodiment of the present invention, one can encourage and train children to drink water when thirsty and to drink sugary drinks only for enjoyment (or as a "treat"). In another example, an athlete can store a sports drink in Dispenser 1, to control the amount of sodium or other nutrient that is delivered to the athlete during a sport activity, while storing and monitoring the consumption of water in Dispenser 49. A dual dispenser combination is preferable for portability; however, a plurality of dispensers can be combined concentrically or non-concentrically to dispense a plurality of different beverages to the user, with each dispenser functioning "monitoring only" mode or "monitoring and control" mode. The user fills Dispenser 1 with beverage 23 as described (FIG. 7) and assembles Dispenser 1 as described (FIG. 6), omitting the attachment of base 5. Lid 56 may be constructed with connection port 62 and switch 58. Liquid level sensor 60 is attached to outer liquid container 51, and is in electronic communication with microprocessor 27, thereby allowing microprocessor 27 to simultaneously monitor and control Dispenser 1, while only monitoring second Dispenser 49. Outer base 55 is constructed of an impact resistant material similar to the material used to construct base 5. Once filled and assembled, and lid confirmed closed through switch 58, Dispenser 1 is attached to second Dispenser 49 though use of inner base 54, by press-fitting, use of threads, or other connection methods known to those skilled in the art, to insert a container 2 fully into inner base 54. Prior to attaching lid 56 to outer liquid container 51, the user can fill outer liquid container 51 with beverage 52 using a gravity-fill method similar to that shown in FIG. 7. Straw 57 is inserted through connection port 63 and lid 56 is threaded to lid assembly 6 and outer liquid container 51 and lid 6 turned until magnet 59 aligns with switch 58, thereby signaling to the microprocessor 27 that Combined Dispenser 50 is ready for use. The operation of Dispenser 50 is similar to that described with respect to FIGS. 8-9.

Referring to FIGS. 11A-B, another alternative embodiment of the present invention, Dispenser 1 is surrounded by Dispenser 69 to form a single dispensing assembly ("Combined Dispenser 69"), such that Dispenser 1 and Dispenser 68 each function independently as described previously with regards to the embodiments shown in FIGS. 1-9 to control the frequency, duration, and rate of flow of a user's intake of beverage 23 (with Dispenser 1) and also similarly control beverage 52 (with Dispenser 68). The assembly, fill procedure, and operation of Combined Dispenser 69 is similar to that of Combined Dispenser 49 (FIG. 10A) except that the lid assembly 65 provides control functionality to both dispensers. For Dispenser 1, illustrating operation of with mouthpiece 4, LRV 25 provides control of beverage 23 through constriction of sleeve 22. For Dispenser 68, illustrating operation with mouthpiece 4, LRV 67 provides control of beverage 52 via constriction of sleeve 66. A dual dispenser combination is a good option for portability. A plurality of dispensers can be combined, concentrically or non-concentrically, to dispense a plurality of different beverages to the user, with Dispenser 1 having monitoring and control capabilities, and all others dispensers each also having monitoring and control capabilities. FIG. 10 illustrates use of straws for both containers, while FIG. 11 illustrates use of mouthpieces for both containers. Any combination of straws and mouthpieces may be used in connection with the embodiments illustrated in FIGS. 10A-B and FIGS. 11A-B. For example, Dispenser 1 can be fitted with a straw and Dispenser 68 can be fitted with a mouthpiece. The embodiments of the present invention, as illustrated by FIGS. 10A-B and FIGS. 11A-B, can utilize any combination of components or features as described with FIGS. 1-9. For example, Dispenser 1 can utilize LRV 26 in addition to, or in place of, LRV 25 to control sip intervals, sip rate and other drink parameters of beverage 23 being consumed by the user from Dispenser 1.

Figure 12A:
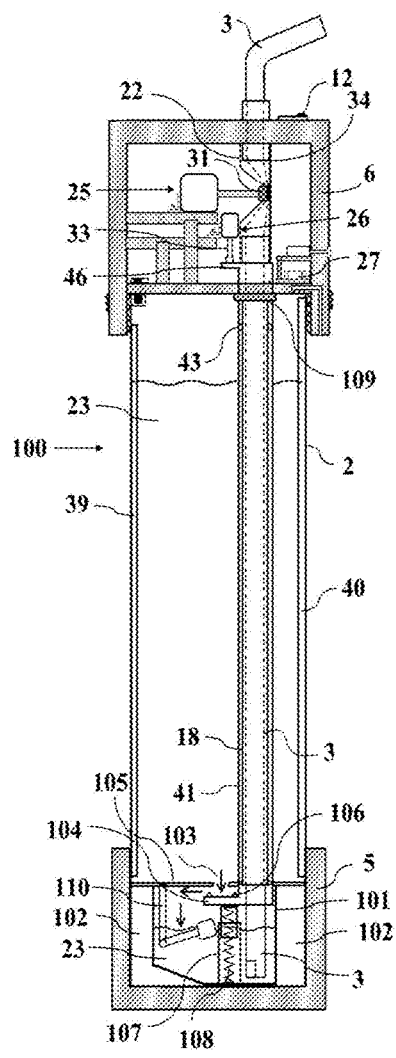
FIG. 12A-C are elevation views of an alternate embodiment of the present invention employing a sip reservoir, with a drinking straw and mouthpiece.
Figure 12B:
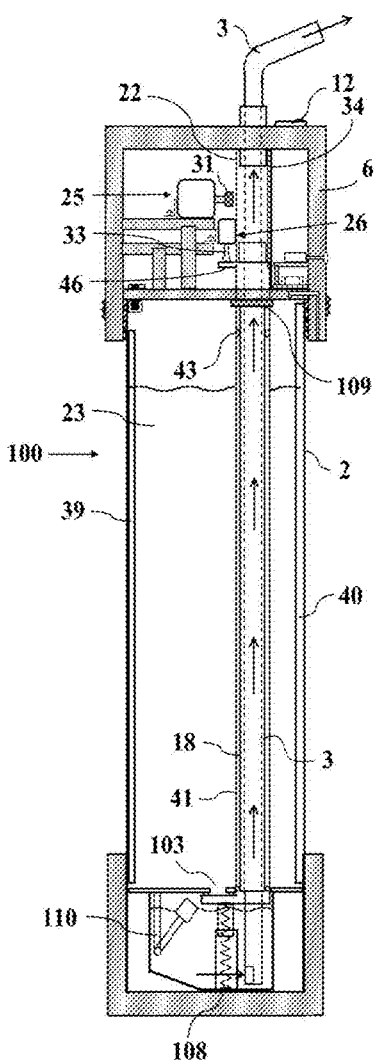

Referring to FIGS. 12A-B, in an alternate embodiment of the present invention, Dispenser 100 is similar to Dispenser 1 as illustrated with FIGS. 1-9, but with inclusion of a sip reservoir 101, omission of spring 42, addition of spring 108, and modification of tube 41 to include an open bottom and addition of lip 104. In this alternate embodiment, LRV 25 controls Sip Rate, Sip Intervals, Sip Duration and Drink Duration. Sip Volume is controlled by LRV 26, which in this embodiment regulates the volume of beverage 23 that is contained in sip reservoir 101. The volume of liquid stored in sip reservoir 101 can be varied between a specified minimum (or "small") volume, for example the Sip Volume associated with a typical young child, and a specified maximum (or "large") volume, for example a Sip Volume associated with a typical adult male. As shown in the drawing, Sip reservoir 101 is cylindrical in shape with a sloped bottom, however it can be other suitable shape. Sip reservoir 101 is fabricated of a material similar to container 2, and is dimensioned to allow containment of a maximum Sip Volume. The bottom of sip reservoir 101 is sloped to allow liquid to accumulate at the entrance to straw 3. Sip reservoir 101 is separated from base 5 by a gap 102 that may be empty or may contain a material, for example a rubber, foam or insulating gel, that can provide added features such as impact dampening and heat insulation. A heat insulating gel can be used to maintain the liquid in sip reservoir 101 in a cold or warm state for a prolonged period of time. Prior to filling container 2 with beverage 23, LRV 26 fully closes orifice 103 by forcing bottom lip 104 against plate 105 and LRV 25 is placed into full-close position by forcing plate 31 against back plate 34 to fully constrict sleeve 22 and straw 3. Upon completion of filling container 2 to the desired volume of liquid based on graduated scale 11 (FIG. 7), top portions of tube 41 and tube 18, that are contained within lid 6, are joined at joint 109 by threaded coupling or other suitable connection method known to those skilled in the art. Tube 18 and tube 41 are open at their distal ends to allow straw 3 to reach the bottom most portion of sip reservoir 101. A spring 108 is attached between bottom of sip reservoir 101 and surface of bottom lip 104, such that spring 108 applies a constant compressive force against bottom lip 104. Spring 108 is enclosed in housing 107, which is comprised of two concentric sliding cylinders. To prevent beverage 23 that is contained in container 2 from entering sip reservoir 101, lip 104 with O-ring 106 is moved linearly toward plate 105 until it is forced firmly against plate 105, causing orifice 103 to be obstructed. Spring 108 is continuously in a compressed state to provide a sufficient force against lip 104 to maintain orifice 103 obstructed or fully closed, such that no liquid is able to pass through orifice 103. To allow beverage 23 that is contained in container 2 to enter sip reservoir 101, lip 104 is moved linearly away from plate 105 until liquid is allowed to pass freely through orifice 103. The linear movement of tube 41 is controlled by LRV 26. To move bottom lip 104 toward plate 105, LRV 26 moves bar 33 lineally away (retracted position) from top lip 46, allowing spring 108 to force lip 104 against plate 105. To move bottom lip 104 away from plate 105 a sufficient distance to allow orifice 103 to fully open, LRV 26 moves bar 33 linearly toward (extended position) top lip 46, applying sufficient force against top lip 46 to overcome the force being applied by spring 108 against bottom lip 104. Sip reservoir 101 is filled by gravity though orifice 103 with a specified volume of beverage 23 that is contained in container 2.

Figure 12C:
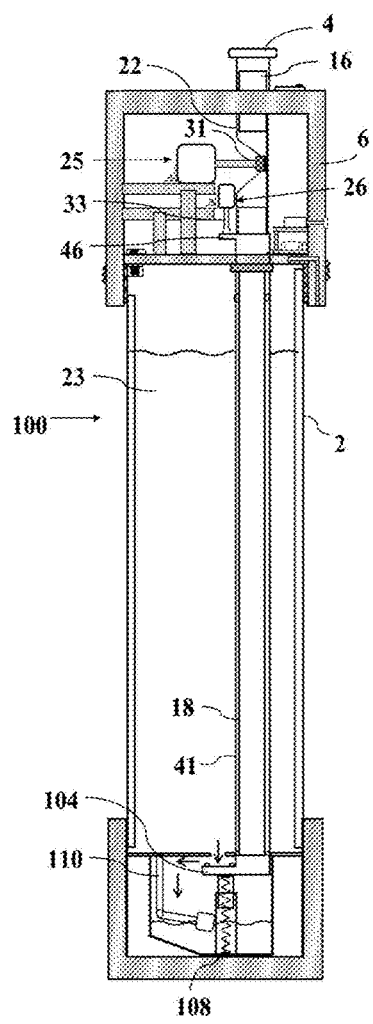

The Sip Volume contained in sip reservoir 101 is controlled by LRV 26 by the change in liquid level in sip reservoir 101, as continuously measured by sensor 110. The sensor 110 can be a float type liquid sensor (as illustrated in FIG. 12A-C) or can be an ultrasound type, optical type, or other suitable level sensor known to those skilled in the art. Referring to FIG. 12A, microprocessor 27 continuously reads the level of liquid in sip reservoir 101 through input signals received from sensor 110. Immediately after LRV 26 opens orifice 103, microprocessor 27 begins to calculate the change in liquid volume stored in container 2. The process of filling sip reservoir 101 with the required Sip Volume is performed with Dispenser 100 oriented in a vertical direction, as can be determined with an attitude sensor. LRV 26 immediately closes orifice 103 when the liquid volume in sip reservoir 101 equals the Sip Volume as set by the user or, for example, as stored by an App contained on the user's wireless device. Once sip reservoir 101 has been filled with the required Sip Volume, and the required sip interval has elapsed, microprocessor 27 illuminates an LED on user interface 12 notifying the user the liquid stored in sip reservoir 101 may be consumed. The user may also receive a notification on user's wireless device. Referring to FIG. 12A, LRV 25 is maintained in the closed position until the required sip interval has elapsed and the user chooses to indicate that he/she is ready to consume the beverage contained in sip reservoir 101 by depressing button 21 (FIG. 5E) on user interface 12 or by making a selection on the App stored on user's wireless device. Once microprocessor 27 receives a signal indicating that the user is ready to consume the liquid, or when sensor 110 records a change in liquid level in sip reservoir 101, it immediately moves LRV 25 to a full open position (FIG. 12B) or partial open position (not shown, but similar to FIGS. 8D-E). It is to be understood that depressing button 21 is not required to initiate a sip, since sensor 110 provides confirmation to microprocessor 27 that the user has begun a sip. The degree of open position is determined by the required sip rate as set by the user or as determined by the App or microprocessor 27. With respect to LRV 25, the sip rate is related to the percent open cross-sectional area of straw 3 or sleeve 22 (in the axial direction). As bar 31 moves closer to back plate 34, straw 3 is further restricted thereby decreasing the percent open area available to transmit liquid flow. After the required sip duration interval has elapsed, microprocessor 27 places LRV 25 in the full closed position and the process of filling sip reservoir 101, with operation of LRV 26, is performed again for the next sip. The process of filling sip reservoir 101 and drinking the liquid stored in sip reservoir 101 is repeated until the total drink duration has expired, liquid level in container 2 approaches zero, or the user or the App on user's device terminates the drink experience. Dispenser 100 can be operated with a straw 3 or mouthpiece 4. Referring to FIG. 12C, in the case of operation with mouthpiece 4, straw 3 is removed and mouthpiece 4 is attached to connection port 16 but tube 18 remains attached between lid 6 and sip reservoir 101.

What is claimed is:

1. An apparatus to regulate the flow of a liquid from a container, the apparatus comprising:
    a container, the container comprising a bottom, a body and a lid, the lid including an opening therethrough, the lid further including an inside, a bottom surface and a top surface;
    a liquid extraction device for removing the liquid from the container, the liquid extraction device comprised of one or more of a group comprised of one or more concentric sleeves, a straw, a tube, and a spout, the liquid extraction device in communication with the liquid and positioned within the lid opening, lid inside, and container;
    a control assembly positioned within the lid or attached to the container, the control assembly including a microprocessor, a sensor and method for estimating the quantity of liquid consumed by the user, one or more liquid regulating valves for regulating the flow of the liquid, an electronic device for communicating with an external computing device, and a source of electrical power for the control assembly, the control assembly regulating the flow of the liquid, dependent on the properties and composition of the liquid and nutritional and health requirements of a user stored within one or more of the group comprised of the control assembly and the external computing device, wherein one or more of the group comprised of the control assembly and the external computing device transmits instructions to the liquid regulating valves to control the flow of the liquid based on the user's intake of nutrients while consuming the liquid and nutrient limits set by the user or the group consisting of the control assembly and the external computing device.

2. The apparatus of claim 1, wherein the external computing device is in communication with the control assembly.

3. The apparatus of claim 1, further comprising a straw that extends through the lid opening and into the container, proximate the container bottom, when the lid is attached to the container body.

4. The apparatus of claim 3, further comprising one or more of a group consisting of an innermost sleeve and one or more concentric outer sleeves, the innermost sleeve positioned within the lid and attached to or surrounding the straw when in straw operation mode or attached to the spout when in spout operation mode, the innermost sleeve in communication with the liquid when attached to the straw or spout or protects components within the lid from leakage of liquid from the straw when surrounding the straw, the one or more outer sleeves surround the innermost sleeve to protect components within the lid from leakage of liquid from the innermost sleeve.

5. The apparatus as described in claim 1, wherein a liquid regulating valves comprises a motor, a bar, a front plate and a back plate, the front plate in communication with the bar and the motor, the bar being driven by the motor, one or more of the group comprised of the innermost sleeve and straw being positioned between the plates, and actuation of the motor causes movement of the bar towards the back plate, constricting one or more of the group comprised of the innermost sleeve and the straw and affecting flow of the liquid from the container, whereby when the bar has been retracted from the back plate such that one or more of the group consisting of the innermost sleeve and the straw is/are sufficiently unconstricted for the liquid to flow fully, the liquid regulating valve is in the full-open position, and wherein the bar has been partially retracted from the back plate such that one or more of the group comprised of the innermost sleeve and the straw is/are partially unconstricted for the liquid to flow partially, the liquid regulating valve is in the partial-open position, and wherein the bar has been extended towards the back plate such that one or more of the group consisting of the innermost sleeve and the straw is/are sufficiently constricted for the liquid not to flow, the liquid regulating valve is in the full-closed position.

6. The apparatus of claim 5, further comprising a second liquid regulating valve to regulate the flow of the liquid, the second liquid regulating valve including a second motor, a second bar, and a second tube, the second tube surrounding the first tube and extending through an opening in the lid bottom surface and into the container, proximate the container bottom when in straw operation mode, or proximate the lid bottom surface when in spout operation mode, the first tube being stationary and second tube slides longitudinally against the first tube, the second bar in communication with the second motor, the second bar being in contact with a top lip of the second tube, and actuation of the second motor causes compressive movement of the second bar on the top lip of the second tube, opening or closing the distal end of one or more of the group comprised of the first tube and the straw and affecting flow of the liquid from the container.

7. The apparatus of claim 2, wherein the external computing device further comprises a microprocessor, and a memory, and the memory includes characteristics of a user, nutritional and health requirements of the user, properties and composition of the liquid, serving size of the liquid, a method for determining the specific quantity of the liquid the user is allowed to consume in a period of time, specific quantity of the liquid consumed by the user, and action to be taken by the control assembly if the specific quantity of the liquid consumed by the user exceeds the specific quantity of the liquid that the user is allowed to consume within the designated period of time.

8. The apparatus of claim 7, wherein the control assembly communicates with the external computing device the specific quantity of liquid consumed by the user, and wherein the external computing device communicates with the control assembly the action to take if the specific quantity of the liquid consumed by the user exceeds the specific quantity of the liquid the user is allowed to consume within the designated period of time, wherein the action comprises adjusting the flow of liquid, the control assembly directing one or more liquid regulating valves to be in full-open position, partial-open position, or full-closed position for a period of time.

9. The apparatus of claim 8, further comprising an input keypad and a status display, the input keypad and status display contained in the container surface, and the input keypad and status display in electronic communication with the microprocessor.

10. The apparatus of claim 9, further comprising:
    a second container, the first container being positioned within the second container; and the second container comprises a bottom, a body and a lid, the lid including an opening therethrough, the lid further including an inside, a bottom surface and a top surface;

a second liquid extraction device for removing the liquid from the second container, the second liquid extraction device comprised of one or more of a group comprised of one or more concentric sleeves, a straw, a tube, and a spout, the second liquid extraction device in communication with the liquid in the second container and positioned within the second container lid opening, second container lid inside, and second container;

a control assembly positioned within the lid or attached to one or more of a group comprised of the first container and the second container, the control assembly including a microprocessor, one or more sensors or method for estimating the quantity of liquid in each container consumed by the user, one or more liquid regulating valves for regulating the flow of liquid in each container, an electronic device for communicating with an external computing device, and a source of electrical power for the control assembly, the control assembly regulating the flow of the fluid in each container, dependent on properties and composition of the fluid in each container and nutritional or health requirements of a user stored within one or more of the group comprised of the control assembly and the external computing device; the apparatus providing any combination of monitoring and control of a plurality of liquids from one or more containers.

11. The apparatus of claim 10, further comprising a second straw that extends through the second container lid opening and into the second container, proximate the second container bottom, when the lid is attached to the second container body.

12. The apparatus of claim 1, wherein the external computing device is chosen from one or more of the group consisting of a keypad in the container lid, a desktop computer, a portable computer, a tablet computer, and a smartphone, each in communication with one or more of the group comprised of the control assembly and the external computing device.

13. The apparatus of claim 9, further comprising:
a second container, the second container positioned below the first container, and the second container comprising a bottom, a body and a top surface, the top surface including first opening therethrough to allow a specific volume of liquid to flow by gravity from the first container to the second container;
a liquid extraction device for removing the liquid from the second container, the liquid extraction device comprised of one or more of a group comprised of one or more concentric sleeves, a straw, and a spout, the liquid extraction device in communication with the liquid in the second container and positioned within the first container lid opening, first container lid inside, first container, and second container;
a first tube, the first tube is attached to the innermost sleeve and extends through an opening in the first container lid bottom surface and through a second opening in the second container top surface and into the second container, wherein the first tube is in communication with the liquid in the second container when not surrounding the straw;
a second tube surrounding the first tube and extending through an opening in the first container lid bottom surface and through the second opening in the second container top surface and into the second container, proximate the second container top surface, the first tube being stationary and second tube allowed to slide axially against the second tube, the second regulating valve creating compressive movement of the second tube to open or close the first opening in the top surface of the second container, a specific quantity of liquid flowing from the first container to the second container through force of gravity when the first opening is maintained open for a period of time, the second container storing a specific volume of liquid for consumption by the user;
a second sensor to measure the quantity of liquid in the second container, the second sensor in communication with the control assembly, the control assembly regulating the specific volume of liquid to be stored in the second container and frequency and flow of liquid to be extracted by the user from the second container, dependent on the properties and composition of the fluid and nutritional and health requirements of a user stored within one or more of the group comprised of the control assembly and the external computing device; and
an attitude sensor, the attitude sensor in communication with the control assembly, the attitude sensor determines whether the container is not in a vertical orientation, and if the container is not in a vertical orientation, the attitude sensor communicates to the liquid regulation valve to prevent the specific volume of liquid from being transferred from the first container to the second container.

14. The apparatus of claim 4, wherein the tube is attached to the innermost sleeve and extends through an opening in the lid bottom surface and into the container, proximate the container bottom when in straw operation mode, or proximate the lid bottom surface when in spout operation mode, wherein the tube is in communication with the liquid when not surrounding the straw.

15. The apparatus of claim 11, further comprising one or more of a group consisting of a second innermost sleeve and one or more second concentric outer sleeves, the second innermost sleeve positioned within the lid and attached to or surrounding the second straw when in straw operation mode or attached to the second spout when in spout operation mode, the second innermost sleeve in communication with the liquid when attached to the second straw or second spout or protects components within the lid from leakage of liquid from the second straw when surrounding the second straw, one or more second outer sleeves surround the innermost second sleeve to protect components within the lid from leakage of liquid from the second innermost sleeve.

16. The apparatus of claim 15, wherein the second tube is attached to the second innermost sleeve and extends through an opening in the lid bottom surface and into the second container, proximate the second container bottom when in straw operation mode, or proximate the lid bottom surface when in spout operation mode, wherein the second tube is in communication with the liquid when not surrounding the second straw.

17. A method to regulate the flow of a liquid from an automatically controlled container, dependent on nutritional and health requirements of a user stored in computing device, wherein the computing device consists of one or more of a group comprised of a microprocessor located within the container and an external computing device, and wherein the container has the capability of regulating the flow of liquid from the container based on instructions received from the computing device, the method comprising the steps of:
creating a user profile for one or more users, the user profile including identifying information for the one or more users, nutritional requirements of the one or more users, quantity of nutritional requirement permitted for each of the one or more users for a specified time period, and storing the user profile within the computing device;

inputting a plurality of nutritional properties of a liquid into the external computing device, wherein the properties and chemical and nutritional composition of the specific liquid are stored within the computing device;

commencing the consumption of the liquid by the user by activating the control assembly computing device using the input device, and the computing device providing instructions to the container to allow the user to commence consumption of the liquid;

measuring or estimating the quantity of liquid and nutrients the user has consumed over a period of time;

determining whether the user has exceeded a maximum quantity of the liquid or one or more nutrients over a period of time;

permitting flow of a specific quantity of the liquid if the maximum quantity of the liquid or one or more nutrients has not been exceeded;

adjusting the flow of the liquid when the maximum quantity of the liquid or one or more nutrients has been exceeded; and repeating the commencing, measuring or estimating, determining, permitting and adjusting steps until the user or computing device provides instructions to the container to terminate the flow of the liquid or until the specified quantity has flowed from the container.

18. The method of claim 17, wherein the nutritional and health requirements include recommended intake over a period of time of water, calories, sugars, vitamins, nutrients, salts, caffeine, and pharmaceutical ingredients of the liquid.

19. The method of claim 18, further comprising the step of determining a nutritional parameter to regulate the flow of the liquid, and transmitting the determining nutritional parameter to the control mechanism.

20. The apparatus of claim 19, further comprising the step of modifying one or more liquid regulating valve when the liquid flow has reached or exceeded the determining nutritional parameter.

* * * * *